(12) United States Patent
Wu et al.

(10) Patent No.: US 9,567,403 B2
(45) Date of Patent: Feb. 14, 2017

(54) BISPECIFIC ANTIBODIES WHICH BIND EGFR AND VEGF

(71) Applicant: BIO-THERA SOLUTIONS, LTD., CO., Guangzhou (CN)

(72) Inventors: Xiaoyun Wu, Guangzhou (CN); Shengfeng Li, Belmont, CA (US); Chenchao Xu, Guangzhou (CN)

(73) Assignee: Bio-Thera Solutions, Ltd., Guangzhou (CN)

( * ) Notice: Subject to any disclaimer, the term of this patent is extended or adjusted under 35 U.S.C. 154(b) by 121 days.

(21) Appl. No.: 14/452,402

(22) Filed: Aug. 5, 2014

(65) Prior Publication Data

US 2015/0044216 A1   Feb. 12, 2015

(30) Foreign Application Priority Data

Aug. 6, 2013  (CN) .......................... 2013 1 0340679

(51) Int. Cl.
| | |
|---|---|
| *C07K 16/22* | (2006.01) |
| *C07K 16/28* | (2006.01) |
| *C07K 16/30* | (2006.01) |
| *A61K 47/48* | (2006.01) |

(52) U.S. Cl.
CPC ......... *C07K 16/30* (2013.01); *A61K 47/48384* (2013.01); *A61K 47/48546* (2013.01); *A61K 47/48561* (2013.01); *A61K 47/48676* (2013.01); *C07K 16/22* (2013.01); *C07K 16/2863* (2013.01); *C07K 2317/31* (2013.01); *C07K 2317/515* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,896,111 | A | 7/1975 | Kupchan et al. |
| 4,137,230 | A | 1/1979 | Hashimoto et al. |
| 4,151,042 | A | 4/1979 | Higashide et al. |
| 4,256,746 | A | 3/1981 | Miyashita et al. |
| 4,260,608 | A | 4/1981 | Miyashita et al. |
| 4,294,757 | A | 10/1981 | Asai |
| 4,313,946 | A | 2/1982 | Powell et al. |
| 4,315,929 | A | 2/1982 | Freedman et al. |

(Continued)

FOREIGN PATENT DOCUMENTS

| | | |
|---|---|---|
| WO | WO-91/06305 | 5/1991 |
| WO | WO-92/01047 | 1/1992 |

(Continued)

OTHER PUBLICATIONS

Carter, P., Bispecific human IgG by design, J. Immmunol. Meth. 248:7-15,2001.*

(Continued)

*Primary Examiner* — Claire Kaufman
(74) *Attorney, Agent, or Firm* — Foley & Lardner LLP

(57) ABSTRACT

Provided are bispecific antibodies having a full-size antibody portion with two light chains and two heavy chains, wherein the two heavy chains each is fused to a single-chain variable fragment (scFv) portion. In certain embodiments, the full-size antibody has specificity to EGFR and the scFv has specificity to VEGF.

2 Claims, 9 Drawing Sheets

(56) References Cited

U.S. PATENT DOCUMENTS

| | | | |
|---|---|---|---|
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,938,949 | A | 7/1990 | Borch et al. |
| 5,639,641 | A | 6/1997 | Pedersen et al. |
| 5,885,793 | A | 3/1999 | Griffiths et al. |
| 5,959,083 | A | 9/1999 | Bosslet et al. |
| 5,969,108 | A | 10/1999 | McCafferty et al. |
| 6,350,860 | B1 | 2/2002 | Buyse et al. |
| 6,511,663 | B1 | 1/2003 | King et al. |
| 6,897,044 | B1 | 5/2005 | Braslawsky et al. |
| 7,129,330 | B1 | 10/2006 | Little et al. |
| 7,195,595 | B2 | 3/2007 | Ling et al. |
| 8,476,409 | B2 * | 7/2013 | Baum ................ C07K 16/2863 |
| 2005/0079170 | A1 | 4/2005 | Le Gall et al. |
| 2005/0100543 | A1 | 5/2005 | Hansen et al. |
| 2005/0163782 | A1 | 7/2005 | Glaser et al. |
| 2009/0148905 | A1 * | 6/2009 | Ashman ............... C07K 16/468 |

FOREIGN PATENT DOCUMENTS

| | | |
|---|---|---|
| WO | WO-92/04053 | 3/1992 |
| WO | WO-94/10202 | 5/1994 |
| WO | WO-95/09917 | 4/1995 |
| WO | WO95/09917 A1 * | 4/1995 |
| WO | WO-97/01580 | 1/1997 |
| WO | WO-98/45332 | 10/1998 |
| WO | WO-99/06587 | 2/1999 |
| WO | WO-00/35956 | 6/2000 |
| WO | WO-01/77342 | 10/2001 |
| WO | WO-2005/000900 | 1/2005 |
| WO | WO-2006/020258 | 2/2006 |
| WO | WO-2007/024715 | 3/2007 |
| WO | WO-2007/080392 | 7/2007 |
| WO | WO-2007/109254 | 9/2007 |
| WO | WO-2009/120922 | 10/2009 |
| WO | WO-2012/145507 | 10/2012 |

OTHER PUBLICATIONS

Ciardiello et al., Interaction between the epidermal growth factor receptor (EGFR) and the vascular endothelial growth factor (VEGF) pathways:a rational approach for multi-target anticancer therapy. Ann Oncol. 17:vii109-14, 2006.*

Cutsem et al., Open label phase III trail of pantitumumab plus best supportive care compared with best supportive care alone in patients with chemotherapy-refractory metastatic colorectal cancer, J. Clin. Oncol. 25(13):1658-1664, May 1, 2007.*

Phillips et al., Targeting HER2-positive breast cancer with trastuzumab-DM1, an antibody-cytotoxic drug conjugate, Canc. Res. 68(22): 9280-9290, Nov. 15, 2008.*

Kontermann et al., Dual targeting strategies with bispecific antibodies, mAbs, 4(2):182-197, Mar./Apr. 2012.*

Berkman et al., "Expression of the vascular permeability factor/vascular endothelial growth factor gene in central nervous system neoplasms", J. Clin. Invest., 1993, 91(1):153-159.

Borgstrom et al., "Complete Inhibition of Angiogenesis and Growth of Microtumors by Anti-Vascular Endothelial Growth Factor Neutralizing Antibody: Novel Concepts of Angiostatic Therapy from Intravital Videomicroscopy", Cancer Res., 1996, 56:4032-4039.

Brown et al., "Expression of vascular permeability factor (vascular endothelial growth factor) and its receptors in adenocarcinomas of the gastrointestinal tract", Cancer Res., 1993, 53:4727-4735.

Carmeliet et al., "Abnormal blood vessel development and lethality in embryos lacking a single VEGF allele", Nature, 1996, 380:435-439.

Cassady et al., "Recent Developments in the Maytansinoid Antitumor Agents", Chem. Pharm. Bull., 2004, 52(1):1-26.

Chari et al., "Immunoconjugates Containing Novel Maytansinoids: Promising Anticancer Drugs", Cancer Res, 1992, 52:127-131.

Dvorak et al., "Vascular Permeability Factor/Vascular Endothelial Growth Factor, Microvascular Hyperpermeability, and Angiogenesis", Am. J. Pathol., 1995, 146(5):1029-1039.

Ferrara et al., "Heterozygous embryonic lethality induced by targeted inactivation of the VEGF gene", Nature, 1996, 380:439-442.

Ferrara et al., "The Biology of Vascular Endothelial Growth Factor", Endocr. Rev., 1997, 18(1):4-25.

Fischer et al., "Bispecific antibodies: molecules that enable novel therapeutic strategies", Pathobiology, 2007, 74(1):3-14.

Hecht et al., "A Randomized Phase IIIb Trial of Chemotherapy, Bevacizumab, and Panitumumab Compared With Chemotherapy and Bevacizumab Alone for Metastatic Colorectal Cancer", J Clin Oncol, 2009, 27:672-680.

Kawai et al., "Chemical Modification of Ansamitocins. III. Synthesis and Biological Effects of 3-Acyl Esters of Maytansinol", Chem. Pharm. Bull., 1984, 32:3441-3451.

Mattern et al., "Association of vascular endothelial growth factor expression with intratumoral microvessel density and tumour cell proliferation in human epidermoid lung carcinoma", Brit. J. Cancer., 1996, 73:931-934.

Melnyk et al., "Vascular Endothelial Growth Factor Promotes Tumor Dissemination by a Mechanism Distinct from Its Effect on Primary Tumor Growth", Cancer Res., 1996, 56:921-924.

Morrison, S.L., "Two heads are better than one", Nature Biotechnology, 2007, 25:1233-1234.

PCT International Preliminary Report on Patentability for Application No. PCT/CN2014/083661 dated Feb. 9, 2016.

PCT International Search Report and Written Opinion for Application No. PCT/CN2014/083661 dated Nov. 18, 2014.

Stanfield et al., "Crystal Structure of a SharkSingle-Domain Antibody V Regionin Complex with Lysozyme", Science, 2004, 305:1770-1773.

Tol et al., "Chemotherapy, Bevacizumab, and Cetuximab in Metastatic Colorectal Cancer", N Engl J Med, 2009, 360:563-72.

Warren et al., "Regulation by vascular endothelial growth factor of human colon cancer tumorigenesis in a mouse model of experimental liver metastasis", J. Clin. Invest., 1995, 95:1789-1797.

Wu et al., "Simultaneous targeting of multiple disease mediators by a dual-variable-domain immunoglobulin", Nature Biotechnology, 2007, 25:1290-1297.

Yu et al., "The biosynthetic gene cluster of the maytansinoid antitumor agent ansamitocin from Actinosynnemapretiosum", PNAS, 2002, 99(12):7968-7973.

Zhang et al., "A dual-targeting antibody against EGFR-VEGF for lung and head and neck cancer treatment", Int J Cancer, 2012, 131(4):956-969.

Brown et al., "Expression of vascular permeability factor (vascular endothelial growth factor) and its receptors in breast cancer", Human Pathol., 1995, 26(1):86-91.

Coloma et al., "Design and production of novel tetravalent bispecific antibodies", Nature Biotechnology, 1997, 15:159-163.

Connolly, "Vascular permeability factor: a unique regulator of blood vessel function", J. Cellular Biochem., 1991, 47(3):219-223.

Ferrara et al., "The vascular endothelial growth factor family of polypeptides", J. Cellular Biochem., 1991, 47:211-218.

Folkman et al., "Angiogenesis Regulation of Angiogenesis in Health & Disease", The Journal of Biological Chemistry, 1992, 267(16):10931-10934.

Greenburg et al., "A new antigen receptor gene family that undergoes rearrangement and extensive somatic diversification in sharks", Nature, 1995, 374:168.

Holliger et al., "Engineered antibody fragments and the rise of single domains", Nature Biotechnology, 2005, 23:1126-1136.

Issel et al., "Maytansine", Cancer Treatment Reviews, 1978, 5(4):199-207.

Kim et al., "Inhibition of vascular endothelial growth factor-induced angiogenesis suppresses tumour growth in vivo", Nature, 1993, 362:841-844.

(56) References Cited

OTHER PUBLICATIONS

Klagsbrun et al.,"Regulators of Angiogenesis", Annu Rev. Physiol., 1991, 53:217-239.
Kupchan et al., "Maytansine, a novel antileukemic ansa macrolide from Maytenus ovatus", J. Am. Chem. Sci, 1972, 94:1354-1356.
Nisonoff et al., "Separation of univalent fragments from the bivalent rabbit antibody molecule by reduction of disulfide bonds", Arch. Biochem. Biophys., 1960, 89:230-244.
Parham, J. "On the fragmentation of monoclonal IgG1, IgG2a, and IgG2b from BALB/c mice", Immunol., 1983, 131(6):2895-2902.
Remillard et al., "Antimitotic activity of the potent tumor inhibitor maytansine", Science, 1975, 189:1002-1005.
Shen et al., "Single variable domain antibody as a versatile building block for the construction of IgG-like bispecific antibodies", Journal of Immunological Methods, 2007, vol. 318, Issues 1-2, pp. 65-74.
Smith et al., "Chemistry and pharmacology of maytansinoid alkaloids", Alkaloids: Chemical and Biological Perspectives, 1984, 2:149-204.
Spinelli et al., "The Crystal Structure of a Llama Heavy Chain Variable Domain", Nature Struct. Biol, 1996, 3:752-757.
Spring et al., "Allotypic Markers on Fab Fragments of Mouse Immunoglobulins", J. Immunol., 1974, 113:470-478.
Widdison et al., "Semisynthetic Maytansine Analogues for the Targeted Treatment of Cancer", J. Med. Chem., 2006, 49:4392-4408.
Wolpert-Defillippes et al., "Initial studies on maytansine-induced metaphase arrest in L1210 murine leukemia cells", Biochem. Pharmacol., 1975, 24(18):1735-1738.

\* cited by examiner

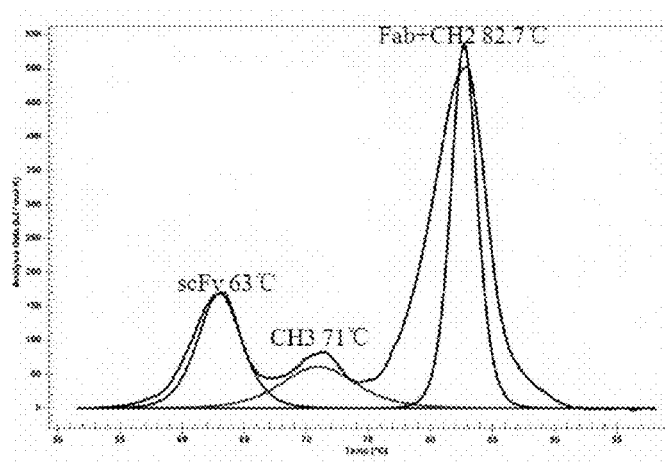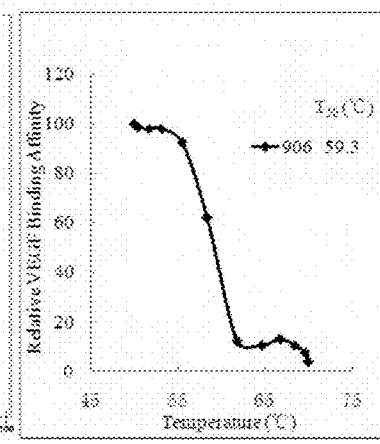
Fig. 3A                    Fig. 3B

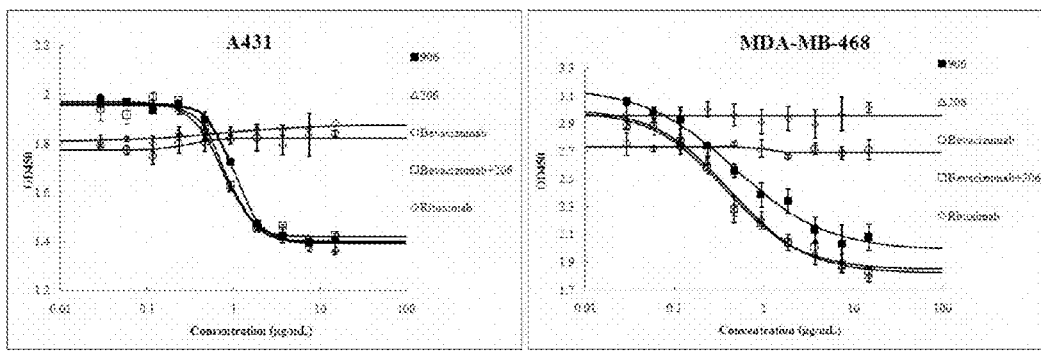
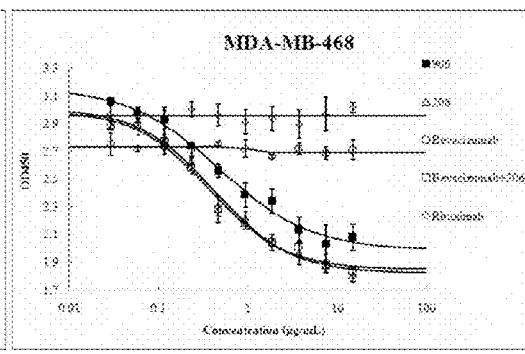
Fig. 5A     Fig. 5B
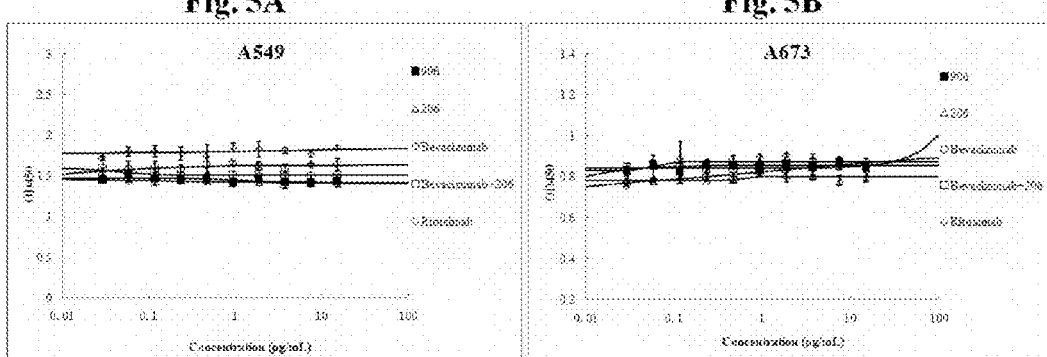
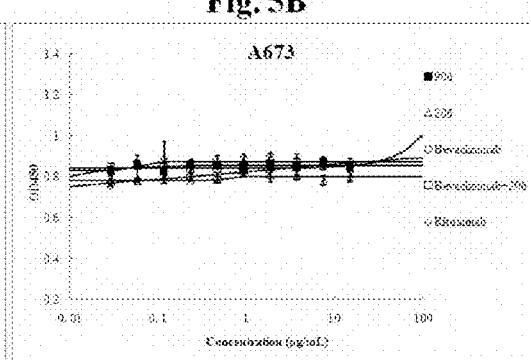
Fig. 5C     Fig. 5D

BISPECIFIC ANTIBODIES WHICH BIND EGFR AND VEGF

CROSS REFERENCE TO RELATED APPLICATION

This application claims priority to Chinese Patent Application No. 201310340679.4, filed Aug. 6, 2013, which is hereby incorporated by reference in its entirety for all of its teachings.

SEQUENCE LISTING

The instant application contains a Sequence Listing which has been submitted electronically in ASCII format and is hereby incorporated by reference in its entirety. Said ASCII copy, created on Oct. 15, 2014, is named 103939-0250_SL.txt and is 27,581 bytes in size.

BACKGROUND

A bispecific antibody (BsAb), or specific monoclonal antibody (BsMAb) is an artificial protein comprised of fragments from two different antibodies. By virtue of the inclusion of two different antigen binding regions, a bispecific antibody is capable of recognizing and binding to two different antigens, or two different epitope on an antigen. In cancer immunotherapy, bispecific antibodies are being developed to simultaneously bind to a cytotoxic cell by targeting a receptor like CD3, and a tumor cell to be destroyed.

Bispecific antibodies present challenges in various aspects. First, they are more difficult to manufacture. Further, the in vitro and in vivo stabilities of these artificial proteins may be questionable. Given the close proximity of the antigen binding regions within a single protein, it also remains to be seen whether the antigen binding regions retain their binding affinities.

In order to overcome manufacturing difficulties, a first-generation BsMAb, called trifunctional antibody, has been developed. It consists of two heavy and two light chains, one each from two different antibodies. The two Fab regions are directed against two antigens. The Fc region (the foot) is made up from the two heavy chains and forms the third binding site; hence the name.

Other types of bispecific antibodies have been designed to overcome certain problems, such as short half-life, immunogenicity and side-effects caused by cytokine liberation. They include chemically linked Fabs, consisting only of the Fab regions, and various types of bivalent and trivalent single-chain variable fragments (scFvs), fusion proteins mimicking the variable domains of two antibodies.

Other types of recombinant antibody formats have also been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Leger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Leger, O., Pathobiology 74 (2007) 3-14). It is important to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

WO 2007/024715 reports dual variable domain immunoglobulins as engineered multivalent and multispecific binding proteins. A process for the preparation of biologically active antibody dimers is reported in U.S. Pat. No. 6,897,044. Multivalent $F_v$ antibody construct having at least four variable domains which are linked with each other via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage or dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

Epidermal growth factor receptor (EGFR) is a transmembrane receptor encoded by the c-erbB 1 proto-oncogene with a molecular weight of approximately 170 kDa. EGFR is normally expressed in a wide variety of epithelial tissues as well as in the central nervous system. Accumulating evidence suggests that the level of EGFR overexpression is an important factor that directly correlates with active proliferation of malignant cells and poor prognosis of patients, thus, providing the rationale for the development of EGFR antagonists as potentially useful therapeutic strategies for the treatment of EGFR-expressing cancers.

EGFR inhibitors encompassing both small molecules and antibodies have been developed for the treatment of cancer.

The small-molecule EGFR tyrosine kinase inhibitors (TKI) erlotinib (Tarceva®) and gefitinib (Iressa®) have demonstrated activity in multiple epithelial tumor types. These compounds reversibly bind to the adenosine triphosphate binding site of the EGFR TKD and inhibit autophosphorylation. Initial results with these molecules as monotherapy or in combination with chemotherapy in unselected populations were disappointing. It is now known that mutations in the EGFR gene alter the tumur phenotype and predict response to treatment, allowing the molecular selection of a subset of patients in which TKI are highly efficacious. The anti-EGFR monoclonal antibodies (mAbs) cetuximab (Erbitux®) and panitumumab (Vectibix®) are established agents in the treatment of CRC (colon and rectal cancer) and SCCHN (Squamous Cell Carcinoma of the Head and Neck). These agents have demonstrated modest clinical efficacy in combination with chemotherapy in phase III trials. However, patients with CRC with KRAS mutations (30%-40% of patients) are unresponsive to cetuximab or panitumumab, when used as monotherapy or in combination with chemotherapy. mAbs targeting cell surface receptors can exert a therapeutic effect either by inhibiting the oncogenic growth signal (blocking ligand binding and/or receptor dimerisation/activation) or through direct cell killing. Cell killing can be achieved by inducing apoptosis in the target cell or cell killing can be achieved by releasing cytotoxic compounds in the target cell through antibody-drug conjugates (ADCs), which consist of cytotoxic agents or toxins chemically conjugated to a monoclonal antibody. Antibody-drug conjugates potentially represent an advantage over treatment with chemotherapy because they are designed to deliver the cytotoxic agent specifically to tumor cells thereby resulting in an improved safety profile.

Angiogenesis is involved in the pathogenesis of a variety of diseases, including solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu Rev. Physiol. 53 (1991) 217-239). Angiogenesis allows the tumor cells to acquire a growth advantage and proliferative autonomy compared to the normal cells. Human vascular endothelial growth factor (VEGF/VEGF-A) is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H., et al., Am. J. Pathol. 146 (1995) 1029-1039).

VEGF is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet, P., et al., Nature, 380 (1996) 435-439; Ferrara, N., et al., Nature, 380 (1996) 439-442; reviewed in Ferrara and Davis-Smyth, Endocrine Rev., 18 (1997) 4-25. The significance of the role played by VEGF has been demonstrated in studies showing that inactivation of a single VEGF allele results in embryonic lethality due to failed development of the vasculature (Carmeliet, P., et al., Nature, 380 (1996) 435-439; Ferrara, N., et al., Nature, 380 (1996) 439-442.

In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara, N., et al., J. Cellular Biochem., 47 (1991) 211-218 and Connolly, J. Cellular Biochem., 47 (1991) 219-223. Alternative mRNA splicing of a single VEGF gene gives rise to five isoforms of VEGF.

Anti-VEGF neutralizing antibodies suppress the growth of a variety of human tumor cell lines in mice (Kim, I., et al., Nature 362 (1993) 841-844; Warren, S. R., et al., J. Clin. Invest. 95 (1995) 1789-1797; Borgstrom, P., et al., Cancer Res. 56 (1996) 4032-4039; and Melnyk, O., et al., Cancer Res. 56 (1996) 921-924). WO 94/10202, WO 98/45332, WO 2005/00900 and WO 00/35956 refer to antibodies against VEGF. Humanized monoclonal antibody bevacizumab (sold under the trade name Avastin®) is an anti-VEGF antibody used in tumor therapy (WO 98/45331).

Bevacizumab, combined with fluoropyrimidine-based chemotherapy is now the standard first-line treatment for metastatic colorectal cancer. Cetuximab, a chimeric IgG1 monoclonal antibody against epidermal growth factor receptor (EGFR), has efficacy as monotherapy and in combination with irinotecan in irinotecan-resistant patients. It would have been expected that the addition of cetuximab to capecitabine, oxaliplatin, and bevacizumab as first-line treatment in patients with metastatic colorectal cancer (the CAIRO2 trial) would achieve better efficacy by blocking both EGFR and VEGF.

However, overall survival and response rates did not improve in the treatment group of combing the two blocking antibodies, cetuximab and bevacizumab. Patients treated with cetuximab who had tumors bearing a mutated KRAS gene had significantly decreased progression-free survival (PFS) as compared with cetuximab-treated patients with wildtype-KRAS tumors (N Engl J Med 2009; 360:563-72).

Panitumumab, a fully human antibody targeting the epidermal growth factor receptor, approved for treatment for patients with metastatic colorectal cancer (mCRC), was evaluated in another trial by adding to bevacizumab and chemotherapy (oxaliplatin- and irinotecan-based) as first-line treatment for mCRC, similar data were obtained. The addition of panitumumab to bevacizumab and oxaliplatin- or irinotecan-based chemotherapy results in increased toxicity and decreased PFS. These simple drug combinations are not recommended for the treatment of mCRC in clinical practice (J Clin Oncol (2009) 27:672-680). Thus, there is an apparent need to a better approach to the treatment of solid tumors by targeting therapeutic agents to the tumor tissues, while simultaneously blocking the signaling pathway by both VEGF and EGFR.

Human domain antibodies selected against VEGF and EGFR were reported by formatting into a dual-targeting IgG (DT-IgG) to directly target both antigens in a single molecule (Int J Cancer. 2012 Aug. 15; 131(4):956-69). This DT-IgG suppressed EGFR positive cell growth, inhibited EGFR activation and induced apoptosis as effectively as cetuximab, and neutralized VEGF as effectively as bevacizumab. However, DT-IgG format is single domain based, and have a very short half-life, and thus is not suitable as therapeutic treatment for cancers.

SUMMARY

The disclosure provides, in one embodiment, bispecific antibodies comprising a full-size antibody portion comprising two light chains and two heavy chains, wherein the two heavy chains each is fused to a single-chain variable fragment (scFv) portion, wherein the full-size antibody has specificity to a first epitope or antigen and the scFv has specificity to a second epitope or antigen that is different from the first epitope or antigen.

In some aspects, the full-size antibody and/or the scFV has specificity to a tumor antigen. Non-limiting examples of tumor antigens include EGFR, Her2, EpCAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP, Tenascin and CD3/TCR antigen.

In one embodiment, provided is a bispecific antibody comprising: (a) a first and a second polypeptides each comprising an immunoglobulin light chain; and (b) a third and a fourth polypeptides each comprising, from the N-terminus to the C-terminus, a variable region, a constant region, and a single-chain variable fragment (scFv), wherein each of the first and second polypeptides, together with each of the variable regions in the third and the fourth polypeptides, form an antigen binding site that specifically recognizes EGFR, and wherein each scFv specifically recognizes VEGF.

In one embodiment, provided is a bispecific antibody comprising: (a) a first and a second polypeptides each comprising an immunoglobulin light chain; and (b) a third and a fourth polypeptides each comprising, from the N-terminus to the C-terminus, a variable region, a constant region, and a single-chain variable fragment (scFv), wherein each of the first and second polypeptides, together with each of the variable regions in the third and the fourth polypeptides, form an antigen binding site that specifically recognizes VEGF, and wherein each scFv specifically recognizes EGFR.

In some aspects, the first and second polypeptides each comprises an amino acid sequence of SEQ ID NO: 1 or an amino acid having at least 90% sequence identity to SEQ ID NO: 1. In some aspects, the third and fourth polypeptides each comprises an amino acid sequence of SEQ ID NO: 2 or an amino acid having at least 90% sequence identity to SEQ ID NO: 2.

Also provided, in one embodiment, is a bispecific antibody comprising two light chains comprising the amino acid sequence of SEQ ID NO: 1 and two heavy chains comprising the amino acid sequence of SEQ ID NO: 2.

In another embodiment, provided is a bispecific antibody comprising a full-size antibody portion comprising two light chains and two heavy chains, wherein the two heavy chains each is fused to a single-chain variable fragment (scFv) portion, wherein the full-size antibody has specificity to EGFR and the scFv has specificity to VEGF.

In some aspects, the antibody is conjugated to a maytansinoid conjugate having Formula Ia, Ib or Ic,

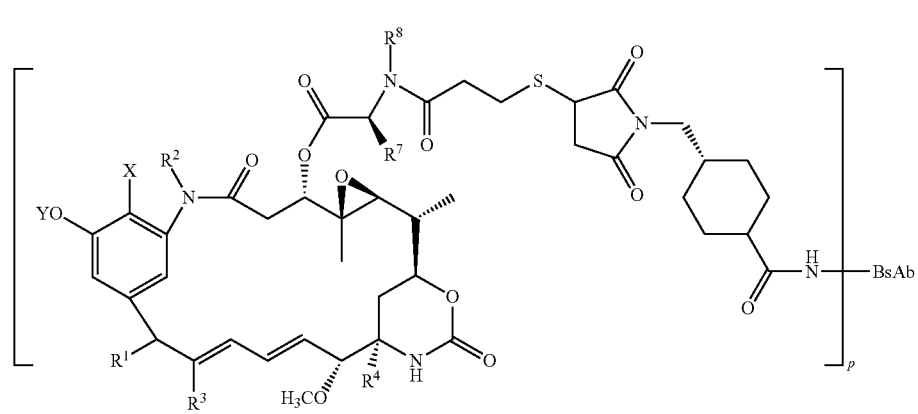

Ia

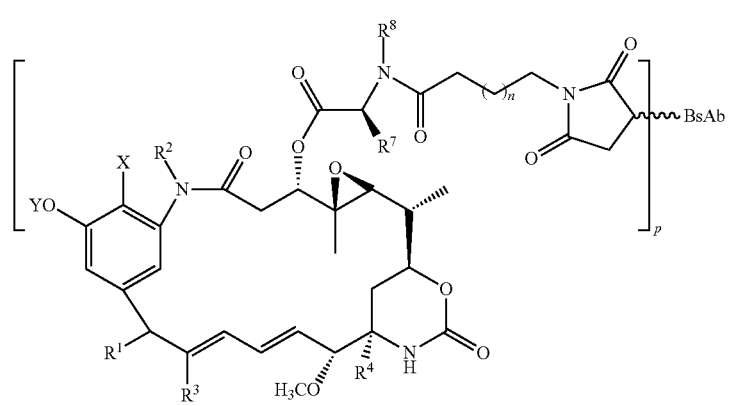

Ib

-continued

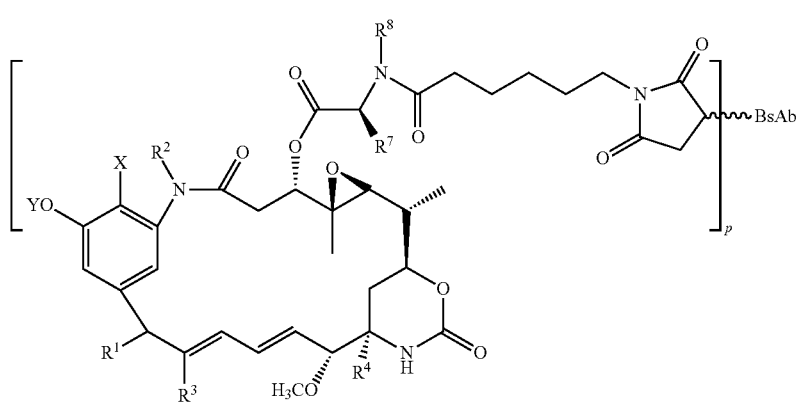

Ic or a pharmaceutically acceptable salt or solvate thereof, wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
n is 0, 1, 2, 3, 4, 5, 6, 7 or 8;
p is selected from 1, 2, 3, 4, 5, 6, 7, 8, 9, 10; and
BsAb denotes a bispecific antibody.

In some aspects, the maytansinoid is conjugated to the bispecific antibody via a linker that is not acid labile, not peptidase cathepsin sensitive, and does not contain a disulfide bond.

Also provided, in one embodiment, is a composition comprising a first polypeptide that comprises the amino acid sequence of SEQ ID NO: 1 and a second polypeptide that comprises the amino acid sequence of SEQ ID NO: 2.

Provided, yet in another embodiment, is a polynucleotide comprising a nucleic acid sequence encoding the amino acid sequence of SEQ ID NO: 2 or an amino acid having at least 90% sequence identity to SEQ ID NO: 2.

One embodiment provides a cell transformed with the polynucleotide of the disclosure.

Methods for treatment and pharmaceutical uses are also provided. In one aspect, provided is a method of treating VEGF related diseases and an EGFR-positive cancer patient, comprising administering to the patient an effective amount of the antibody of the disclosure.

In yet other embodiments, provided are methods for preparing a bispecific antibody derived from a first, IgG2, antibody, and a second antibody. The IgG2 antibody can be modified to include constant regions from an IgG1 antibody. Polynucleotides with such modifications can then be transformed into a cell, allowing production of the bispecific antibody.

Thus, in one embodiment, provided is a bispecific antibody derived from a first, IgG2, antibody and a second antibody having specificity to a different epitope, comprising (a) a first and a second polypeptides each comprising the immunoglobulin light chain of the first antibody; and (b) a third and a fourth polypeptides each comprising, from the N-terminus to the C-terminus, the variable region of the first antibody, an IgG1 constant region, and a single-chain variable fragment (scFv) derived from the second antibody.

BRIEF DESCRIPTION OF THE DRAWINGS

FIG. 3A depicts the DSC results of Antibody 906. FIG. 3B shows the thermal challenge assay result of Antibody 906.

FIG. 5A shows the cell proliferation inhibitory assay result of Antibody 906 in A431 cells. FIG. 5B shows the cell proliferation inhibitory assay result of Antibody 906 in MDA-MB-468 cells. FIG. 5C shows the cell proliferation inhibitory assay result of Antibody 906 in A549 cells. FIG. 5D shows the cell proliferation inhibitory assay result of Antibody 906 in A673 cells.

DETAILED DESCRIPTION

I. Definitions

Figure 1A:
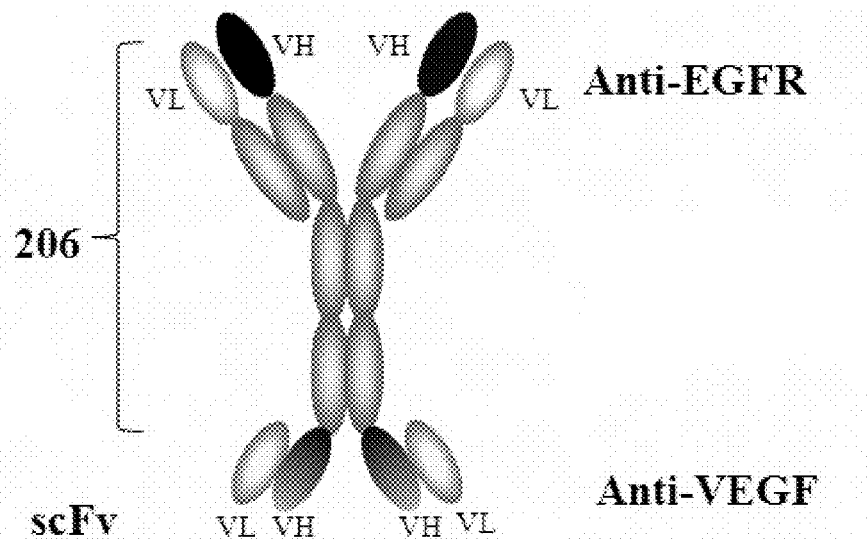
FIG. 1A shows the molecular structure of Antibody 906.

As used herein, the following definitions shall apply unless otherwise indicated.

As used herein, unless otherwise stated, the singular forms "a," "an," and "the" include plural reference. Thus, for example, a reference to "a compound" includes a plurality of compounds.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% or plus or minus 5%, or plus or minus 1% of the particular term.

As used herein, the term "comprising" is intended to mean that the compositions and methods include the recited elements, but not excluding others. "Consisting essentially of" when used to define compositions and methods, shall mean excluding other elements (e.g., protein domains or fragments) of any essential significance to the combination. For example, a polypeptide consisting essentially of the domains or fragments as defined herein would not exclude other domains or fragments (e.g., linkers) that do not materially affect the basic and novel characteristic(s) of the polypeptide. "Consisting of" shall mean excluding more than trace amount of other ingredients and substantial method steps recited. Embodiments defined by each of these transition terms are within the scope of this disclosure.

As used herein, "antibody (Ab)" or "antigen binding unit (Abu)" refers to a molecule, such as a protein, that contains one or more antigen-binding sites. The term encompasses full antibodies and antibody fragments, without limitation. In some aspects, an antibody includes heavy chain variable domains (VH) and/or an antibody light chain variable domains (VL), or pairs of VH/VL, and can be derived from whole antibodies or antibody fragments such as single chain Fv, a VH domain and/or a VL domain, Fab, or (Fab)$_2$. In some aspects, each of the antigen-binding sites includes an antibody heavy chain variable domain (VH) and/or an antibody light chain variable domain (VL), and can be formed by a pair of polypeptides that include an antibody light chain variable domain (VL) and an antibody heavy chain variable domain (VH).

"Bispecific antibodies" refer to antibodies which bind to two different antigens or two different epitopes, which can be present in the same antigen or in different antigens. By contrast, a "monospecific" antibody can have one or more binding sites, but each of them binds to the same epitope.

The term "valent" denotes the presence of a specified number of binding sites in an antibody. As such, the terms "bivalent", "tetravalent", and "hexavalent" denote the presence of two binding sites, four binding sites, and six binding sites, respectively, in an antibody. In this context, a bispecific antibody is at least "bivalent" but can be "trivalent" or "multivalent," e.g., tetravalent or hexavalent. In some aspects, a bispecific antibody is bivalent, trivalent or tetravalent. In some aspects, the bispecific antibody is bivalent. In some aspects, the bispecific antibody is trivalent. In some aspects, the bispecific antibody is tetravalent.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell.

The term "variable domain", when used in reference to a domain of a heavy chain or a light chain, refer respectively to the portion of a heavy chain or a light chain which is involved directly in binding the antibody to the antigen. The variable domains of human light and heavy chains have the same general structure and each domain comprises four framework (FR) regions whose sequences are widely conserved, connected by three "hypervariable regions" (or complementarity determining regions, CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site.

The terms "hypervariable region" or "antigen-binding portion of an antibody", when used herein, refers to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. scFv molecules are known in the art and are described, e.g., in U.S. Pat. No. 5,892,019.

As used herein, "maytansinoid" refers to a maytansine analogue, including stereoisomers thereof. Maytansine can be isolated from plants of the genus *Maytenus* U.S. Pat. No. 3,896,111). It is of the formula:

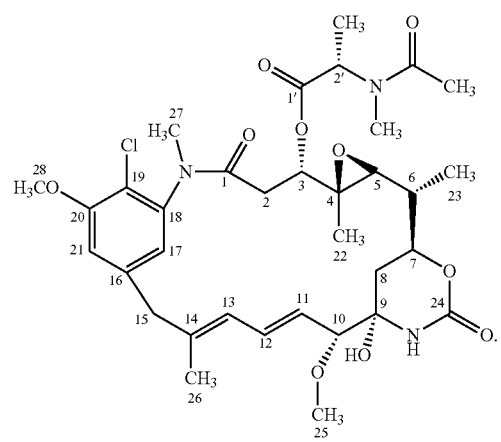

Maytansinoids are compounds having the ring structure of maytansine with one or more modifications of the substituents on the ring.

"Alkyl" refers to monovalent saturated aliphatic hydrocarbyl groups having from 1 to 10 carbon atoms and preferably 1 to 6 carbon atoms. $C_v$ alkyl wherein v is an integer represents an alkyl having v carbons. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl (CH₃CH₂CH₂CH₂—), isobutyl ((CH₃)₂CHCH₂—), sec-butyl ((CH₃)(CH₃CH₂)CH—), t-butyl ((CH₃)₃C—), n-pentyl (CH₃CH₂CH₂CH₂CH₂—), and neopentyl ((CH₃)₃CCH₂—). "Alkylene" is a divalent saturated aliphatic hydrocarbyl groups having from 1 to 10 carbon atoms and preferably 1 to 6 carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH₂C≡CH).

"Amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' and R" is hydrogen but not both. When referring to a disubstituted amino, it is meant that neither R' and R" are hydrogen.

"Amino acid" refers any compound, whether natural, unnatural or synthetic, which includes both an amino group and a carboxy group. Examples of amino acid include, but are not limited to glycine (NH₂CH₂COOH), cysteine, alanine, N-methyl-L-alanine, including both the D and L optical isomers. "Amino acid side chain" refers to the substituent that replaces a hydrogen of the methylene group of glycine or glycine derivatives, such as N-alkylglycine or glycine esters. Examples of an amino acid side chain include, but are not limited to the side chains of the natural amino acids, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Carbonyl" refers to the divalent group —C(O)— which is equivalent to —C(=O)—.

"Carboxy" or "carboxyl" refers to —COOH or CO₂H or salts thereof.

"Carboxylic acid" refers to a compound having at least one carboxy.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl:

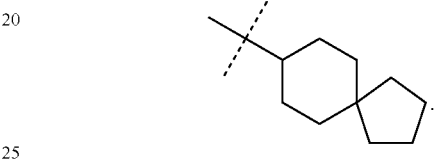

"Cycloalkylene" refers to a cyclic alkylene.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Substituted alkyl," "substituted alkenyl," "substituted alkynyl," "substituted cycloalkyl," "substituted cycloalkenyl," "substituted aryl," "substituted heteroaryl" or "substituted heterocyclic" refers to alkyl, alkenyl, alkynyl, cycloalkyl, cycloalkenyl, aryl, heteroaryl or heterocyclic groups, respectively, which are substituted with 1 to 5, preferably 1 to 3, or more preferably 1 to 2 substituents selected from the group consisting of alkyl, halo alkyl, —O—$R^{20}$, —S—$R^{20}$, alkenyl, alkynyl, —C(=O)$R^{20}$, —C(=S)$R^{20}$, —C(=O)O$R^{20}$, —$NR^{20}$C(=O)$R^{21}$, —OC(=O)$R^{21}$, —$NR^{20}R^{20}$, —C(=O)$NR^{20}R^{20}$, —C(=S)$NR^{20}R^{20}$, —$NR^{20}$C(=O)$NR^{20}R^{20}$, —$NR^{20}$C(=S)$NR^{20}R^{20}$, —OC(=O)$NR^{20}R^{20}$, —SO$_2$$NR^{20}R^{20}$, —OSO$_2$$NR^{20}R^{20}$, —$NR^{20}$SO$_2$$NR^{20}R^{20}$)—C(=$NR^{20}$)$NR^{20}R^{20}$, aryl, —$NR^{20}$C(=O)O$R^{21}$, —OC(=O)O$R^{21}$, cyano, cycloalkyl, cycloalkenyl, —$NR^{20}$C(=$NR^{20}$)$NR^{20}R^{20}$, halo, hydroxy, heteroaryl, heterocyclic, nitro, —SO$_3$H, —SO$_2$$R^{21}$, and —OSO$_2$$R^{21}$, wherein each $R^{20}$ is selected from the group consisting of hydrogen, alkyl, alkenyl, alkynyl, aryl, cycloalkyl, cycloalkenyl, heteroaryl, and heterocyclic or two $R^{20}$ with the atom(s) bound thereto form a heterocyclic ring, and $R^{21}$ is selected from the group consisting of alkyl, alkenyl, alkynyl, aryl, cycloalkyl, cycloalkenyl, heteroaryl, and heterocyclic.

"Nitro" refers to the group —NO$_2$.

"Oxo" refers to the atom (=O) or (—O$^-$).

"Spiro ring systems" refers to bicyclic ring systems that have a single ring carbon atom common to both rings.

"Thiol" refers to the group —SH.

"Thiocarbonyl" refers to the divalent group —C(S)— which is equivalent to —C(=S)—.

"Thione" refers to the atom (=S).

"Compound" or "compounds" as used herein is meant to include the stereoisomers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Solvate" refer to an association of a solvent with a compound, in the crystalline form. The solvent association is typically due to use of the solvent in the synthesis, crystallization, and/or recrystallization of the compound. "Solvate" includes hydrate which is an association of water with a compound, in the crystalline form.

"Patient" or "subject" refers to mammals and includes humans and non-human mammals.

"Pharmaceutically acceptable salt" refers to pharmaceutically acceptable salts of a compound, which salts are derived from a variety of organic and inorganic counter ions well known in the art and include, by way of example only, when the molecule contains an acidic functionality, salts of organic or inorganic bases, such as sodium, potassium, calcium, magnesium, ammonium, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and tetraalkylammonium, and the like; and when the molecule contains a basic functionality, salts of organic or inorganic acids, such as hydrochloride, hydrobromide, tartrate, mesylate, acetate, maleate, and oxalate. Other non-limiting examples of acids include sulfuric acid, nitric acid, phosphoric acid, propionic acid, glycolic acid, pyruvic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease.

An "effective amount" is intended to mean an amount of an active compound or pharmaceutical agent that elicits the biological or medicinal response in a tissue, system, animal, individual or human that is being sought by a researcher, veterinarian, medical doctor or other clinician, which includes treating a disease.

II. Bispecific Antibodies

The present disclosure, in one embodiment, provides a bispecific antibody that shows significantly improved manufacturing efficiency and stability, along with high binding affinity and tumor therapeutic effects in vivo. Such properties are unexpected given the perceived low manufacturing efficiency and deteriorated stability and therapeutic efficacy associated with bispecific antibodies.

In one embodiment, the bispecific antibody of the present disclosure includes a full-size antibody portion having specificity to a first antigen, fused to a single-chain variable fragment (scFv) portion having specificity to a second antigen. In some aspects, the first antigen is EGFR and the second antigen is VEGF. It is also contemplated that the first antigen is VEGF and the second antigen is EGFR.

A "full-size antibody" or "full-size antibody" refers to an antibody or antibody portion that includes at least two light chains and two heavy chains, and each heavy chain includes at least a variable region (e.g., VH) and three constant regions (e.g., CH1, CH2, and CH3).

With reference to FIG. 1A, a bispecific antibody of the present disclosure can include four polypeptides, two relatively long peptide polypeptides and two light chains. This bispecific antibody can also be viewed as a full-size antibody fused to a single-chain variable fragment (scFv) portion. The upper, full-size portion of the bispecific antibody includes two light chains and two heavy chains and can target EGFR, as illustrated. The lower, scFv portion can target VEGF, as illustrated.

As experimental data show below, such an anti-EGFR/VEGF bispecific antibody shows significantly improved manufacturing efficiency and stability as well as high binding affinity and tumor therapeutic effects in vivo, as compared to other bispecific antibodies known in the art.

It is noted that in the antibody illustrated in FIG. 1A, the full-size antibody portion of each of the long polypeptides is derived from an IgG2 antibody, but is modified to include an IgG1 constant region. Accordingly, each long polypeptide includes, from the N-terminus (top) to the C-terminus (bottom), a variable region, an IgG1 constant region, and a scFv that includes a VH and a VL fragments.

The IgG1 constant region, it is contemplated, improves the bispecific antibody's ability to induce antibody-dependent cell-mediated cytotoxicity (ADCC). Examples of IgG1 constant regions that mediate improved ADCC are known in the art (see, e.g., Stewart et al. Protein Eng Des Sel. 24(9):671-8, 2011).

In some aspects, each of the first antigen and/or the second antigen is a tumor antigen.

A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP, Tenascin and CD3/TCR antigen.

In some aspects, the first antigen and the second antigen are EGFR and VEGF, respectively, or vice versa.

In some aspects, the IgG1 constant region and the scFv are linked by a linker, such as a short peptide. The linker is typically five to about 30 amino acid residues in length. In some aspects, the linker is from about 10 to about 25 amino acid residues in length. The linker can be rich in glycine for flexibility, as well as serine or threonine for solubility. In some aspects, each of the linkers includes at least 50% glycine, or even at least 60%, 70%, 80%, or 90% glycine.

In some aspects, each of the light chain, variant region, IgG1 constant region, scFv VH and VL are human sequences, optionally with modifications.

In some aspects, in the bispecific antibody each of the light chains contains an amino acid sequence of SEQ ID NO: 1 or a sequence that has at least about 80%, 85%, 90%, 95%, 98% or 99% sequence identity to SEQ ID NO: 1.

In some aspects, in the bispecific antibody each of the long polypeptides contains an amino acid sequence of SEQ ID NO: 2 or a sequence that has at least about 80%, 85%, 90%, 95%, 98% or 99% sequence identity to SEQ ID NO: 2.

TABLE 1

Amino acid sequence of the light chains of
an anti-EGFR and anti-VEGF bispecific antibody SEQ ID NO: 1 (1-214)-Anti-EGFR light chain
DIQMTQSPSSLSASVGDRVTITCQASQDISNYLNWYQQKPGKAPKLLIYD
ASNLETGVPSRFSGSGSGTDFTFTISSLQPEDIATYFCQHFDHLPLAFGG
GTKVEIKRTVAAPSVFIFPPSDEQLKSGTASVVCLLNNEYPREAKVQWKV TABLE 1 -continued Amino acid sequence of the light chains of
an anti-EGFR and anti-VEGF bispecific antibody

DNALQSGNSQESVTEQDSKDSTYSLSSTLTLSKADYEKHKVYACEVTHQG
LSSPVTKSFNRGEC

TABLE 2

Amino acid sequence of the long polypeptide
of an anti-EGFR and anti-VEGF bispecific antibody SEQ ID NO: 2 (1-712)
Anti-EGFR Variable Region (1-117 447)
QVQESGPGLVKPSETLSLTCTVSGGSVSSGDYYWTWIRQSPGKGLEWIGH
IYYSGNTNYNPSLKSRLTISIDTSKTQFSLKLSSVTAADTAIYYCVRDRV
TGAFDIWGQGTLVTVSS Constant Region (118-447)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLEPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK Linker 1 (448-462)
GGGGSGGGGSGGGGS Anti-VEGF heavy chain varaible region (463-585)
EVQLVESGGGLVQPGGSLRLSCAASGYDFTHYGMNWVRQAPGKCLEWVGW
INTYTGEPTYAADFKRRFTFSLDTSKSTAYLQMNSLRAEDTAVYYCAKYP
YYYGTSHWYFDVWGQGTLVTVSS Linker 2 (586-605)
GGGGSGGGGSGGGGSGGGGS Anti-VEGF light chain varaible region (606-712)
DIQLTQSPSSLSASVGDRVTITCSASQDISNYLNWYQQKPGKAPKVLIYF
TSSLHSGVPSRFSGSGSGTDFTLTISSLQPEDFATYYCQQYSTVPWTFGC
GTKVEIK The anti-EGFR and anti-VEGF antibody portions of the bispecific can also be derived from other antibodies. For instance, Table 3 provides the sequences of Cetuximab and Nimotuzumab, two anti-EGFR antibodies.

TABLE 3

Anti-EGFR antibodies suitable for preparing
bispecific ligands

Cetuximab Light Chain (SEQ ID NO: 3)
DILLTQSPVILSVSPGERVSFSCRASQSIGTNIHWYQQRTNGSPRLLIKY
ASESISGIPSRFSGSGSGTDFTLSINSVESEDIADYYCQQNNNWPTTFGA
GTKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGA Cetuximab heavy Chain (SEQ ID NO: 4)
QVQLKQSGPGLVQPSQSLSITCTVSGFSLTNYGVHWVRQSPGKGLEWLGV
IWSGGNTDYNTPFTSRLSINKDNSKSQVFFKMNSLQSNDTAIYYCARALT
YYDYEFAYWGQGTLVTVSAASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKRVEPKSPKSCDKTHTCPPCPAPELLGGPSVFLFPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSP
GK Nimotuzumab Light Chain (SEQ ID NO: 5)
DIQMTQSPSSLSASVGDRVTITCRSSQNIVHSNGNTYLDWYQQTPGKAPK
LLIYKVSNRFSGVPSRFSGSGSGTDFTFTISSLQPEDIATYYCFQYSHVP

TABLE 3 -continued

Anti-EGFR antibodies suitable for preparing bispecific ligands

WTFGQGTKLQITREVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

Nimotuzumab Heavy Chain (SEQ ID NO: 6)
QVQLQQSGAEVKKPGSSVKVSCKASGYTFTNYYIYWVRQAPGQGLEWIGG
INPTSGGSNFNEKFKTRVTITADESSTTAYMELSSLRSEDTAFYFCTRQG
LWFDSDGRGFDFWGQGTTVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVP The full-size and scFv antibody portions of the bispecific can also be derived from other antibodies. For instance, Table 4 provides the light chain/heavy chain sequences of a number of antibodies, which can be adopted to prepare the full-size portion, or further modified to prepare the scFv portion.

In some aspects, the bispecific antibody includes a full-size antibody portion comprising two light chains having the amino acid sequence of SEQ ID NO: 7, 9, 11, or 13, and two heavy chains having the amino acid sequence of SEQ ID NO: 8, 10, 12, or 14, respectively. In some aspects, these bispecific antibody have a scFv portion having specificity to EGFR.

In some aspects, the bispecific antibody includes a scFv portion comprising two light chain variable regions derived from the amino acid sequence of SEQ ID NO: 7, 9, 11, or 13, and two heavy chain variable regions derived from amino acid sequence of SEQ ID NO: 8, 10, 12, or 14, respectively. In some aspects, these bispecific antibody have a full-size antibody portion having specificity to EGFR.

TABLE 4

Antibody light and heavy chains suitable for preparing the full-size portion or scFv portion of bispecific ligands Bevacizumab (anti-VEGF) light chain (SEQ ID NO: 7)
DIQMTQSPSSLSASVGDRVTITCSASQDISNYLNWYQQKPGKAPKVLIYF
TSSLHSGVPSRFSGSGSGTDFTLTISSLQPEDFATYYCQQYSTVPWTFGQ
GTKVEIK Bevacizumab heavy chain (SEQ ID NO: 8)
EVQLVESGGGLVQPGGSLRLSCAASGYTFTNYGMNWVRQAPGKGLEWVGW
INTYTGEPTYAADFKRRFTFSLDTSKSTAYLQMNSLRAEDTAVYYCAKYP
HYYGSSHWYFDVWGQGTLVTVSS Anti-VEGF antibody A light chain (SEQ ID NO: 9)
DIQMTQSPSSLSASVGDRVTINCQASQSIYNNNELSWYQQKPGKPPKLLI
YRASTLASGVPSRFSGSGSGTDFTLTISSLQPEDVATYYCGGYKSYSNDG
NGFGGGTKVEIK Anti-VEGF antibody A heavy chain (SEQ ID NO: 10)
EVQLVESGGGLVKPGGSLRLSCAASGFSFSNNDVMCWVRQAPGKGLEWIG
CIMTTDVVTEYANWAKSRFTVSRDSAKNSVYLQMNSLRAEDTAVYFCARD
SVGSPLMSFDLWGPGTLVTVSS Anti-VEGF antibody B light chain (SEQ ID NO: 11)
DIQMTQSPSSLSASVGDRVTITCRASQGIRNDLGWYQQKPGKAPKRLIYA
ASSLQSGVPSRFSGSGSGTEFTLTISSLQPEDFATYYCLQHNSYPPVYTF
GQGTKLEIKR Anti-VEGF antibody B heavy chain (SEQ ID NO: 12)
QVQLVQSGAEVKKPGASVKVSCKASGYTFTSYDINWVRQATGQGLEWMGW
MNPNSGNTGYAQKFQGRVTMTRNTSISTAYMELSSLRSEDTAVYYCARGG
YSSSWYYWYFDLWGRGTLVTVSS

TABLE 4 -continued

Antibody light and heavy chains suitable for preparing the full-size portion or scFv portion of bispecific ligands Anti-VEGF antibody C light chain (SEQ ID NO: 13)
DIQMTQSPSSLSASVGDRVTITCRASQDVSTAVAWYQQKPGKAPKLLIYS
ASFLYSGVPSRFSGSGSGTDFTLTISSLQPEDFATYYCQQSYTTPPTFGQ
GTKVEIKR Anti-VEGF antibody C heavy chain (SEQ ID NO: 14)
EVQLVESGGGLVQPGGSLRLSCAASGETISDYWLHWVRQAPGKGLEWVAG
ITPAGGYTYYADSVKGRFTISADTSKNTAYLQMNSLRAEDTAVYYCARFV
FFLPYAMDYWGQGTLVTVSS Modifications to an antibody chain can be made, up to about 1%, 2%, 5%, 10%, 15%, 20% or 25%, while retaining its activity. Nucleotide and amino acid sequence modifications are known that do not affect or alter the above-mentioned characteristics of the antibody. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, a predicted non-essential amino acid residue in a bispecific antibody can be replaced with another amino acid residue from the same side chain family.

Also provided, in some embodiments, are polynucleotides encoding any of the polypeptides, DNA constructs containing one or more or all polynucleotides encoding these polypeptides, and cells enclosing such polynucleotides or DNA constructs.

The antigen-binding sites of the bispecific antibody, such as heavy chain variable domains (VH) and/or antibody light chain variable domains (VL) can be derived a) from known antibodies, such anti-EGFR antibodies including Cetuximab, Panitumumab, or nimotuzumab, b) from new antibodies obtained e.g., by de novo immunization methods known in the art.

Likewise, the scFv portion of the bispecific antibody can be derived from known antibodies. For instance, Kim et al., Nature 362 (1993) 841-844; Warren, R. S., et al., J. Clin. Invest. 95 (1995) 1789-1797; Borgstrom, P., et al., Cancer Res. 56 (1996) 4032-4039; Melnyk, O., et al., Cancer Res. 56 (1996) 921-924). WO 94/10202, WO 98/45332, WO 2005/00900, WO 00/35956 and US 2007/0141065 describe anti-VEGF antibodies.

The bispecific antibodies are at least monovalent, better as bivalent, and may be trivalent, tetravalent or multivalent. Preferably the bispecific antibody according to the invention is bivalent, trivalent or tetravalent.

A further aspect of the disclosure is a nucleic acid molecule encoding the bispecific antibody.

The disclosure further provides an expression vector which comprises the nucleic acid according to the invention and which is capable of expressing the nucleic acid in a prokaryotic or eukaryotic host cell.

Also provided are host cells containing such vectors for the recombinant production of an antibody according to the invention.

The disclosure further provides a prokaryotic or eukaryotic host cell comprising a vector according to the invention.

The disclosure further provides a method for the production of a bispecific antibody according to the invention, comprising expressing a nucleic acid according to the invention in a prokaryotic or eukaryotic host cell and recovering the bispecific antibody from the cell or the cell culture supernatant. The invention comprises the antibody obtained by such a recombinant method. The invention further comprises the methods or processes by which the bispecific antibody is purified and prepared, such size exclusion chromatography, ion exchange chromatography.

Amino acid sequences of the various domains/regions or chain of the bispecific antibody can be adopted from known antibodies (e.g., Cetuximab, Panitumumab, Nimotuzumab, Matuzumab, for EGFR), or can be derived de novo.

For instance, for an anti-EGFR and anti-VEGF bispecific antibody, the anti-EGFR and/or anti-VEGF regions and chains can include fragments of antibodies (polyclonal and monoclonal) such as Fab, Fab', F(ab')$_2$, and Fv (see, e.g., Parham, J. Immunol. 131:2895-2902 (1983); Spring et al., J. Immunol. 113:470-478 (1974); Nisonoff et al., Arch. Biochem. Biophys. 89:230-244 (1960)); domain antibodies (dAbs) and antigen-binding fragments thereof, including camelid antibodies (see, e.g., Desmyter et al., Nature Struct. Biol, 3:752 (1996)); shark antibodies called new antigen receptors (IgNAR) (see, e.g., Greenberg et al., Nature, 374:168 (1995); Stanfield et al. Science 305:1770-1773 (2004)).

Monoclonal antibody techniques allow for the production of anti-EGFR and/or anti-VEGF antibodies in the form of specific monoclonal antibodies. Particularly well known in the art are techniques for creating monoclonal antibodies produced by immunizing mice, rabbits, or any other mammal with the antigen of interest such as the tumor specific antigens isolated from the target cell. Another method of creating anti-EGFR and/or anti-VEGF antibody is using phage libraries of scFv (single-chain variable region), specifically human scFv (see, e.g., Griffiths et al., U.S. Pat. Nos. 5,885,793 and 5,969,108; McCafferty et al., WO 92/01047; Liming et al., WO 99/06587), or domain antibodies using yeast selection system (see, e.g., U.S. Pat. No. 7,195,595). In addition, resurfaced antibodies such as those disclosed in U.S. Pat. No. 5,639,641 may also be used, as may chimerized or humanized antibodies.

Selection of a particular anti-EGFR and/or anti-VEGF antibody depends upon the disease type, cells and tissues that are to be targeted. In some embodiments, the anti-EGFR and/or anti-VEGF antibodies are human monoclonal antibodies.

III. Conjugation to Maytansinoids

In some embodiments, the bispecific antibody is conjugated with a maytansinoid molecule or a maytansinoid derivative (sometimes referred to as a "drug"), thus targeting disease cells or tissues while simultaneously inhibiting tumor angiogenesis. Such conjugation to the antibody exerts a cytotoxic, cytostatic, or immunosuppressive effect on the antigen-expressing cells. The high affinity of the antibody drug conjugate ensures that the cytotoxic maytansinoid targets the tumor cells.

In some aspects, the maytansinoid is linked to the bispecific antibody via a linker that is not acid labile, not peptidase cathepsin sensitive, and does not contain a disulfide bond. Such linkers are contemplated to provide stability to the conjugated molecule prior to endocytosis, such as during circulation, to premature degradation of the linker and release of the toxic drug, thus minimize the toxic effect of the drug. In some embodiments, the maytansinoid-linker portion of the conjugate is N2'-deacetyl-N2'-(6-maleimido-1-oxo-hexyl)-maytansine (3AA-MDC or batansine), or a derivative thereof.

Maytansinoids are highly cytotoxic compounds which inhibit the formation of microtubule protein polymerization (Remillard, et al., Science 189, 1002-1005 (1975)). Maytansine was first isolated by Kupchan et al. (J. Am. Chem. Sci 94:1354-1356 (1972)) from the east African shrub *Maytenus serrata*. Maytansinoids including maytansinol and C-3 esters of maytansinol were also produced by certain microbes (U.S. Pat. No. 4,151,042). Various analogues of maytansinol with different cytotoxicity have also been prepared by synthetic chemistry (for review see Chem. Pharm. Bull. 52(1) 1-26 (2004)). Examples of mytansinoids include maytansine, mertansine (MD1), MD3 and MD4. Maytansine is a strong mitotic inhibitor and shows significant inhibitory activity against multiple tumors including Lewis lung carcinoma and B-16 melanocarcinoma solid murine tumor models. Maytansine was reported to inhibit the human acute lymphoblastic leukemia line C.E.M. at concentrations as low as $10^{-7}$ g/mL (Wolpert-DeFillippes et al., Biochem. Pharmacol. 1735-1738 (1975)). It also showed to be 100- to 1000-fold more cytotoxic than conventional chemotherapeutic agents like methotrexate, daunorubicin, and vincristine (U.S. Pat. No. 3,896,111).

Ansamitocins, the bacterial maytansinoids, show an activity spectrum and effective dosage range similar to maytansine. They inhibit P388 leukemia at daily doses as low as 0.8 g/kg. Ansamitocin P3 (AP3) was also shown to be effective against multiple cancer cell lines (for review see Alkaloids, vol. 2, 149-204 (1984); Chem. Pharm. Bull. 52(1) 1-26 (2004)). The maytansinol C-3 esters with N-methyl-L-alanine derivatives are found to be much more cytotoxic than the corresponding esters of simple carboxylic acid and to be 100 times more cytotoxic than their epimers corresponding to N-methyl-D-alanine (U.S. Pat. Nos. 4,137,230; 4,260,608; Kawai, et al., Chem. Pharm. Bull. 32: 3441-3451 (1984); Widdison, et al., J. Med. Chem. 49: 4392-4408 (2006)).

Maytansinoids were expected to have the capacity to treat many different cancers due to their highly toxic nature and the in vitro activities against multiple cancer cell lines. However, the toxicity also made this class of compounds not favorable in human clinical trials as the side effects were intolerable for many patients (Issel et al., 5 Cancer Treat. Rev. 199-207 (1978)). Accordingly, targeted delivery of cytotoxic compounds to cancer cells by conjugating toxic drugs to monoclonal antibodies (ADC for antibody drug conjugate) is proposed in order to reduce the side effects. Certain conjugates of cytotoxic drugs such as maytansinoids, auristatins, anthracyclins, duocarmycins, etc. with antibodies are being evaluated in preclinical or clinical studies in the treatment of diseases.

Antibody drug conjugates (ADCs) are composed of three key elements: antibody, linker, and drug. The selection of a particular antibody and drug will have a great impact on the efficacy and safety depending on the particular disease. Linker stability and the method by which the drug is conjugated to the antibody play a critical role in the success or failure of the ADC drug development.

The efficacy of an ADC depends in part on combination of a variety of parameters, involving not only the specificity of the antibody and the potency of drugs, but also the linker's stability or sensitivity to cleavage, the cell surface triggered the internalization, trafficking, and subsequent release of the active cytotoxic payload. Thus, ADC comprising different drug linkers or with different antibodies against the same target can vary significantly in their utility.

In some embodiments, provided is a method for conjugating a maytansinoid compound to an mono-specific antibody, bi-specific antibody, or multi-specific antibody, wherein the antibody is first partially reduced, and the light chain and heavy are separated, maytansinoid compound is linked to the light chain via a linker, then the conjugated light chain is mixed with heavy chains under oxidizing conditions. Such conjugation methods are contemplated to provide chain specific conjugation to antibody molecules, such as the modification of Fc domain is minimal, thus minimize the effect on the functions of Fc domain, including ADCC and the FcRn binding.

In some embodiments, the maytansinoid conjugate is of Formula Ia, Ib or Ic.

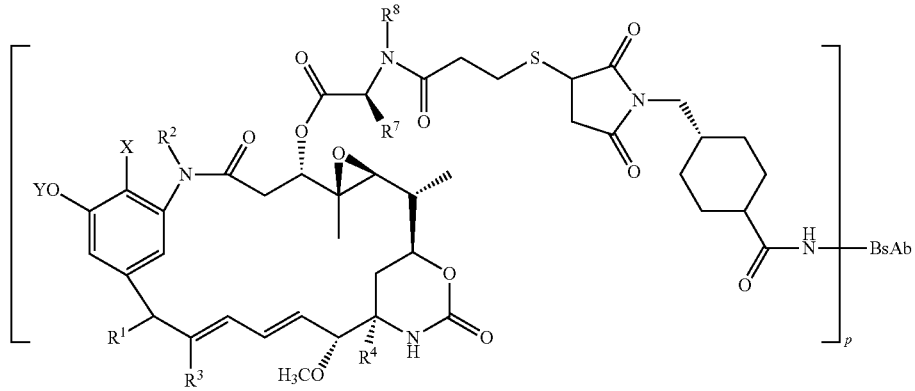

Ia

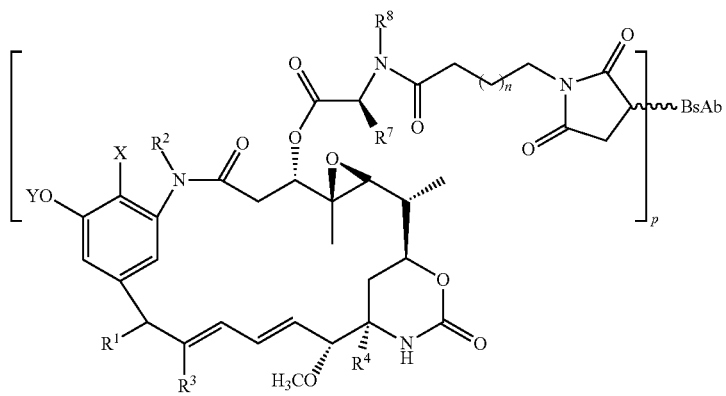

Ib

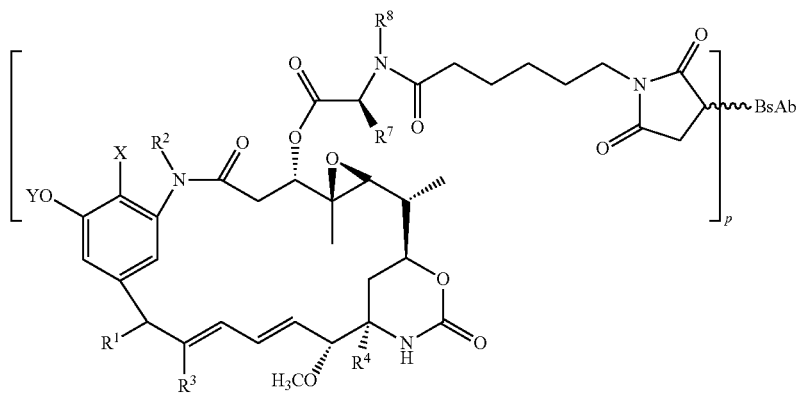

Ic or a pharmaceutically acceptable salt or solvate thereof, wherein

X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;

$R^5$ is $C_1$-$C_6$ alkyl or benzyl;

$R^6$ is $C_1$-$C_6$ alkyl, phenyl or benzyl;

$R^7$ is hydrogen, $C_1$-$C_6$ alkyl or an amino acid side chain;

$R^8$ is hydrogen or $C_{1-6}$ alkyl;

n is 0, 1, 2, 3, 4, 5, 6, 7 or 8;

p is selected from 1, 2, 3, 4, 5, 6, 7, 8, 9, 10; and

BsAb denotes a bispecific antibody.

In some aspects, the maytansinoid conjugated to a bispecific antibody is via a linker that is not acid labile, not peptidase cathepsin sensitive, and does not contain a disulfide bond.

Maytansinoids suitable for conjugating to a bispecific antibody include maytansinol and maytansinol analogues and can be isolated from natural sources according to known methods, produced using biotechnologies (see e.g., Yu et al., 99 PNAS 7968-7973 (2002)), or prepared synthetically according to known methods (see e.g., Cassady et al., Chem. Pharm. Bull. 52(1) 1-26 (2004)).

Non-limiting examples of suitable maytansinol analogues include:

(1) C-19-dechloro (U.S. Pat. No. 4,256,746) (prepared by LAH reduction of ansamytocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using lithium aluminium hydride (LAH));

(3) C-20-demethoxy, C-20-acyloxy (—OCOR), +/−dechloro (U.S. Pat. No. 4,294,757) (prepared by acylation using acyl chlorides);

(4) C-9-SH (U.S. Pat. No. 4,424,219) (prepared by the reaction of maytansinol with $H_2S$ or $P_2S_5$);

(5) C-14-hydroxymethyl ($CH_2OH$) or acyloxymethyl ($CH_2OC(=O)$phenyl or $CH_2OC(=O)(C_1$-$C_5$ alkyl)) (U.S. Pat. No. 4,331,598) (prepared from *Nocardia*);

(6) C-15-hydroxy/acyloxy (U.S. Pat. No. 4,364,866) (prepared by the conversion of maytansinol by *Streptomyces*);

(7) C-15-methoxy (U.S. Pat. Nos. 4,313,946 and 4,315,929) (isolated from Trewia nudlflora);

(8) C-18-N-demethyl (U.S. Pat. Nos. 4,362,663 and 4,322,348) (prepared by the demethylation of maytansinol by *Streptomyces*); and (9) 4,5-deoxy (U.S. Pat. No. 4,371,533) (prepared by the titanium trichloride/LAH reduction of maytansinol).

Many positions on maytansinol can be useful as the linkage position, depending upon the type of linker. For example, for forming an ester linkage, the C-3 position having a hydroxyl group, the C-14 position modified with hydroxymethyl, the C-15 position modified with a hydroxyl group and the C-20 position having a hydroxyl group are all suitable. In some embodiments, the linkage position is the C-3 position.

In some embodiments, provided herein is a maytansinoid conjugated to a bispecific antibody through a linker, of Formula Ia, Ib or Ic:

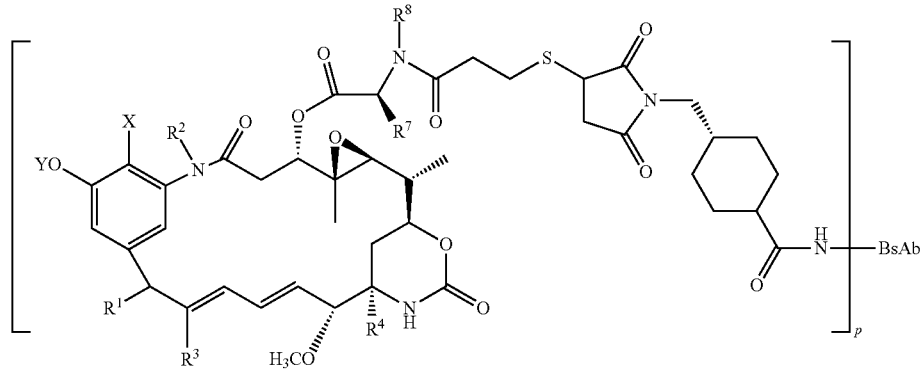

Ia

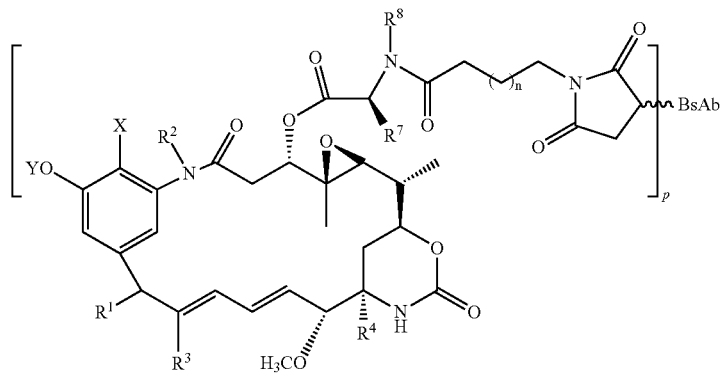

Ib

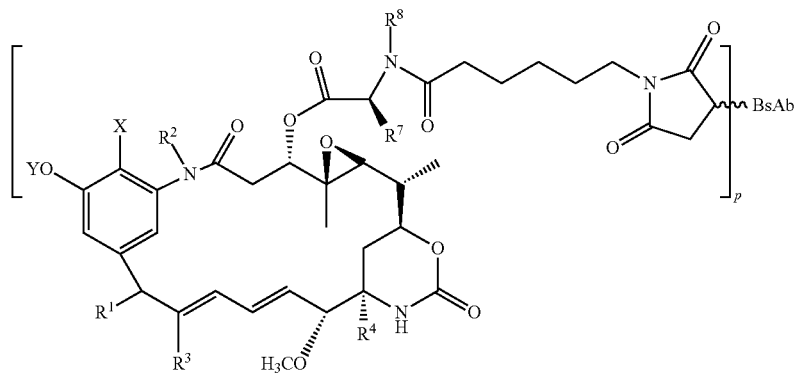

or a pharmaceutically acceptable salt or solvate thereof, wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —$CH_2$OH, or —$CH_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
n is 0, 1, 2, 3, 4, 5, 6, 7 or 8;
p is selected from 1, 2, 3, 4, 5, 6, 7, 8, 9, 10; and
BsAb denotes a bispecific antibody.

In some embodiments, the compound of Formula Ia is

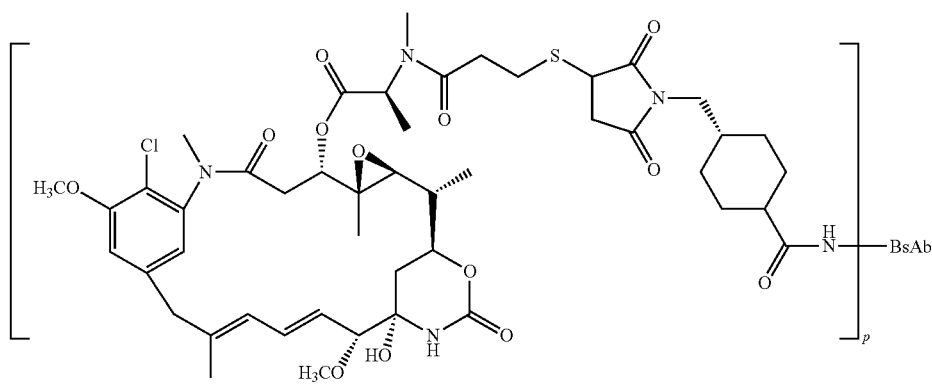

or a pharmaceutically acceptable salt or solvate thereof, wherein BsAb denotes a bispecific antibody.

In some embodiments, the compound of Formula Ib or Ic is

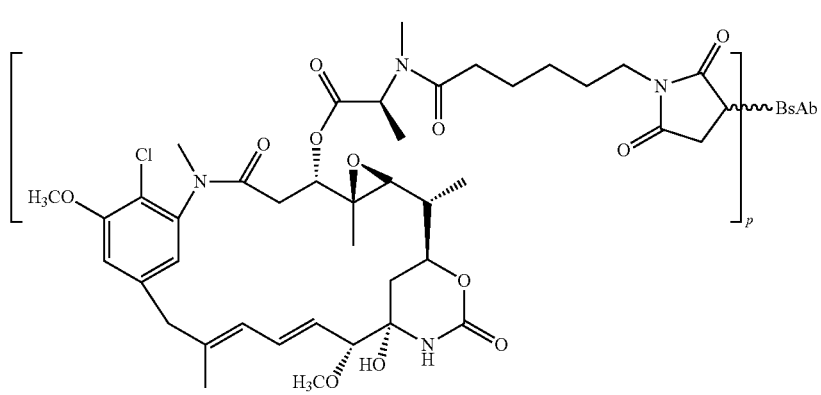

or a pharmaceutically acceptable salt or solvate thereof, wherein BsAb denotes a bispecific antibody.

In some aspects, the linker includes a disulfide bond. In this respect, the maytansinoid-linker-antibody conjugate has improved circulation stability and minimized prematurely release of toxic drug molecule that causes side effects such as bystander killing effects on non-targeted cells.

Examples of conjugates having a linker comprising a disulfide bond include compounds of Formula Id:

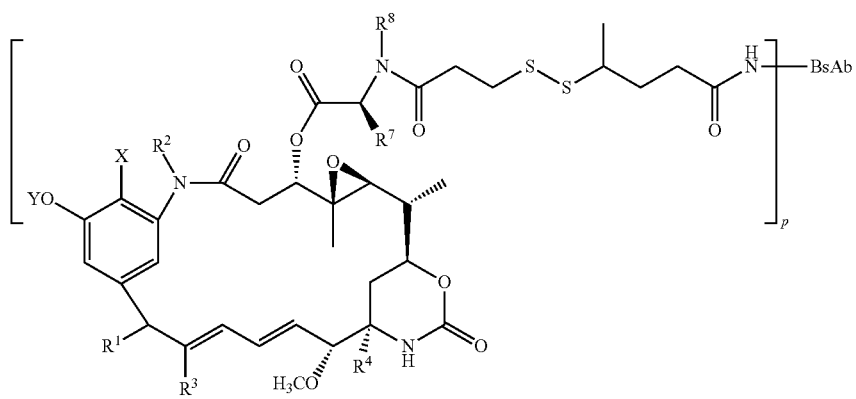

or a pharmaceutically acceptable salt or solvate thereof, wherein
X is hydrogen or halo;
Y is selected from the group consisting of hydrogen, $C_1$-$C_6$ alkyl, $C_3$-$C_6$ cycloalkyl, and —C(=O)$R^5$;
$R^1$ is selected from the group consisting of hydrogen, —OH, —OC(=O)$R^5$ and —O$R^5$;
$R^2$ is hydrogen or $C_1$-$C_6$ alkyl;
$R^3$ is methyl, —CH$_2$OH, or —CH$_2$C(=O)$R^6$;
$R^4$ is —OH or —SH;
$R^5$ is $C_1$-$C_6$ alkyl or benzyl;
$R^6$ is $C_1$-$C_6$ alkyl, phenyl or benzyl;
$R^7$ is hydrogen, $C_1$-$C_6$ alkyl or an amino acid side chain;
$R^8$ is hydrogen or $C_{1-6}$ alkyl;
p is selected from 1, 2, 3, 4, 5, 6, 7, 8, 9, 10; and
BsAb denotes a bispecific antibody.

A particular example of compounds of Formula Id is a compound of Formula IId.

a puromycin, a dolastatin, and a vinca alkaloid. Other suitable cytotoxic agents include anti-tubulin agents, such as an auristatin, a vinca alkaloid, a podophyllotoxin, a taxane, a baccatin derivative, a cryptophysin, a maytansinoid, a combretastatin, or a dolastatin. In some embodiments, the cytotoxic agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-3, DM-4, or eleutherobin. Suitable immunosuppressive agents include, for example, gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist. In some embodiments, the cytotoxic agent is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, DM-3, DM-4, or netropsin.

The drug of the conjugates can also be substituted by a suitable immunosuppressive agent, for example, gancyclo-

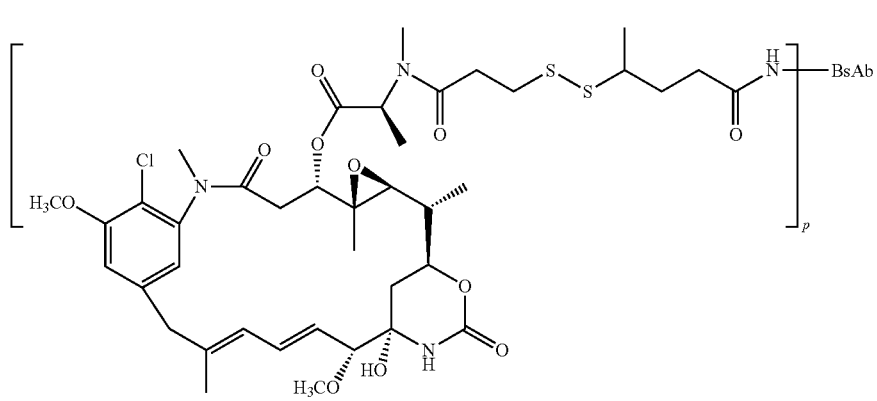

or a pharmaceutically acceptable salt or solvate thereof, wherein BsAb denotes a bispecific antibody.

The drug of the conjugates can be substituted by other suitable cytotoxic agents, for example, an auristatin, a DNA minor groove binding agent, a DNA minor groove alkylating agent, an enediyne, a lexitropsin, a duocarmycin, a taxane, vir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-lipoxygenase inhibitor, or a leukotriene receptor antagonist.

Methods of Preparing the Conjugates

A bispecific antibody can be modified with appropriate bifunctional modifying agent. In some embodiments, a group comprising a thiol (SH) group (also referred to as thio-comprising group) can be introduced to the side-chain of an amino acid residue, such as the side-chain of a lysine, on the bispecific antibody. For example, the amino group of a lysine residue on the bispecific antibody can be converted to a thiol-comprising group by reaction with 2-iminothiolane (Traut's Reagent), or with N-succinimidyl 3-(2-pyridyldithio) propanoate (SPDP), N-succinimidyl 4-(2-pyridyldithio) butanoate (SPDB), etc and followed by reduction with a reducing reagent, such as 2-mercaptoethanol, dithiothreitol (DTT) or tris(2-carboxyethyl)phosphine (TCEP).

Non-limiting examples of thiol-comprising groups that can replace the side-chain amino group of a lysine residue include $-NHC(=NH)(CH_2)_n-SH$ and $-NHC(O)(CH_2)_n-SH$, wherein n is 1, 2, 3, 4, 5 or 6. When a thiol-comprising group is introduced to an amino acid residue, the amino acid residue is referred to as thiolated amino acid. For example, when the side-chain amino group of a lysine residue is converted to a thio-comprising group, the lysine residue is referred to as thiolated lysine. The number of free thiol (SH) group introduced in a bispecific antibody may vary, such as between 1 and about 20, or 5 to 15, and or 5 to 12. The linkers or drug-linkers can form bonds with the free thiol (SH) group of a thiolated lysine residue on the bispecific antibody. In some embodiments, the number of linkers or drug-linkers that form bonds with thiolated lysine residues in the bispecific antibody is between 1 and about 10. In some embodiments, the number of such formed bonds is at least 1, or alternatively at least 2, or 3, or 4, or 5. In some embodiments, the number of such formed bonds is no more than 10, or alternatively no more than 9, or 8, 7, 6, 5, or 4. In some embodiments, each bispecific antibody, on average, is conjugated with 3-5 drug molecules.

In another embodiment, a drug-linker can be conjugated to a bispecific antibody by binding to the thiol group of a cysteine residue. Each bispecific antibody typically contains multiple cysteines, but many, if not all, of them form disulfite bonds between each other, and thus are not available for such conjugation. In some embodiments, therefore, one or more of the disulfite bonds of the bispecific antibody can be broken to form free thiol (SH) groups by reaction with a reducing reagent, such as 2-mercaptoethanol, dithiothreitol (DTT) or tris(2-carboxyethyl)phosphine (TCEP), for instance. The reaction can be monitored and/or controlled so that a sufficient number of disulfite bonds are broken to allow conjugation while maintaining a sufficient number of disulfide bonds to keep the structure stability of the bispecific antibody.

In some aspects, the maytansinoid or maytansinoid derivative is conjugated to the light chain only, thus forming chain-specific drug conjugation. In one embodiment, the light chain can be modified with appropriate bifunctional modifying agent. In some embodiments, a group comprising a thiol (SH) group (also referred to as thio-comprising group) can be introduced to the side-chain of an amino acid residue, such as the side-chain of a lysine, on the light chain (short chain). For example, the amino group of a lysine residue on the short chain can be converted to a thiol-comprising group by reaction with 2-iminothiolane (Traut's Reagent), or with N-succinimidyl 3-(2-pyridyldithio) propanoate (SPDP), N-succinimidyl 4-(2-pyridyldithio) butanoate (SPDB), etc and followed by reduction with a reducing reagent, such as 2-mercaptoethanol, dithiothreitol (DTT) or tris(2-carboxyethyl)phosphine (TCEP).

In some embodiments, the number of bonds formed between the drug-linker and cysteine residue on the bispecific antibody or a particular chain, or subunit of the bispecific antibody, is from 1 to 10. In one embodiment, the number of such bonds is at least 1, or alternatively at least 2, or 3, or 4, or 5. In some embodiments, the number of such formed bonds is no more than 10, or alternatively no more than 9, or 8, 7, 6, 5, or 4. In one embodiment, each bispecific antibody, on average, is conjugated with 3-5 drug molecules through cysteines.

In some embodiments, drug molecules are conjugated to the bispecific antibody through a mixture of lysine and cysteine residues.

A bispecific antibody can be modified, by way of, e.g., site-specific mutagenesis, to introduce additional thiolated lysine or cysteine residues to allow suitable conjugation. Amino acid modification methods are well known in the art. Modified bispecific antibodies can then be experimentally examined for their stability and antigen binding capability. In one embodiment, at least one thiolated lysine or cysteine residue is introduced by such modification. In another embodiment, at least two thiolated lysine or cysteine residues are introduced by such modification.

The amount of the maytansinoid or maytansinoid derivative conjugated to the bispecific antibody may vary depending on many factors, such as the potency of the maytansinoid or maytansinoid derivative, the size, stability of the bispecific antibody, conjugatable groups available on the bispecific antibody, etc. In some embodiments, 1 to 10 maytansinoid molecules are conjugated with a bispecific antibody. In some embodiments, an average of 3 to 5 maytansinoid molecules are conjugated with a bispecific antibody. In some embodiments, an average of 3.5 maytansinoid molecules are conjugated with a bispecific antibody.

IV. Methods of Treatment

The present disclosure further provides, in one embodiments, methods of treating a proliferative, inflammatory or immunologic disease or condition in a patient in need thereof. The method entails administering an effective amount of a bispecific antibody of the present disclosure. In some aspects, the disease is cancer, such as bladder cancer, lung cancer, breast cancer, melanoma, colon and rectal cancer, non-Hodgkin lymphoma, endometrial cancer, pancreatic cancer, kidney cancer, prostate cancer, leukemia, thyroid cancer, lung cancer, esophageal cancer, and head and neck cancer.

The bispecific antibody can be formulated as pharmaceutical compositions and administered to the patient in a variety of forms adapted to the chosen route of administration, i.e., orally or parenterally, by intravenous (I.V.), intramuscular, topical or subcutaneous routes. The amount of the compounds will vary depend on the nature of the drug, linker, drug load, degree of cell surface triggered the internalization, trafficking, and release of the drug, the disease being treated, the conditions of the patient, such as age, gender, weight, etc. and can be determined by methods known to the art, for example, see U.S. Pat. No. 4,938,949, and will be ultimately at the discretion of the attendant physician or clinician.

In general, a suitable dose will be in the range of from about 0.1 to about 200 mg/kg, e.g., from about 0.5 to about 50 mg/kg of body weight I.V. infusion over 30-90 min every 1-4 week for 52 weeks, about 1.0 to about 25 mg/kg of body weight IV infusion over 30-90 min every 1-4 week for 52 weeks, about 1.5 to about 15 mg/kg body weight IV infusion over 30-90 min every 1-4 week for 52 weeks, or in the range of about 1 to 10 mg/kg body weight IV infusion over 30-90 min every 1-4 week. In some embodiments, the dose is from about 1.0 mg to about 100 mg/day, e.g., from about 2 mg to about 5 g per day, about 10 mg to about 1 g per day, about 20 to about 500 mg per day, or in the range of about 50 to 100 mg per day. The compounds can be administered daily, weekly, monthly, such as once a day, every 1-3 weeks, or month. Alternatively, the compounds can be administered in cycles, such as administered daily for a number of days, for example, 5 days to 21 days, with a period, such as one day to seven days, wherein no antibody is being administered.

In some embodiments, the antibody is administered at an initial dose of 1-4 mg/kg over 30-90 minute IV infusion, followed by 1-2 mg/kg over 30 minute I.V. infusion weekly or every 1-4 weeks for 52 weeks. In some embodiments, the compound is administered at an initial dose of 2-10 mg/kg over 30-90 minutes I.V. infusion, followed by 1-5 mg/kg over 30-90 minutes IV infusion every 1-4 weeks for 52 weeks.

In some embodiments, the antibodies are administered in conjunction with another therapy. For example, the compounds can be co-administered with another therapy for treating cancer, for example, radiation therapy or another anticancer agent known in the art.

V. Pharmaceutical Compositions

In a further aspect, provided are pharmaceutical compositions comprising one or more bispecific antibodies of the present disclosure, and one or more pharmaceutically acceptable carriers. Such compositions should contain at least 0.1% of bispecific antibodies. The percentage of the bispecific antibodies may vary and may be between about 2 to about 90% of the weight of a given unit dosage form. The amount of bispecific antibodies in such therapeutically useful compositions is such that an effective dosage level will be obtained.

Examples of pharmaceutical compositions suitable for injection or infusion can include sterile aqueous solutions or dispersions in a pharmaceutically acceptable liquid carrier or vehicle, or sterile powders comprising the active ingredient which are adapted for the extemporaneous preparation of sterile injectable or infusible solutions or dispersions, optionally encapsulated in liposomes. Other forms of pharmaceutical compositions include topical formulations, such as gel, ointments, creams, lotions or transdermal patches, etc. The pharmaceutical compositions include using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

In a further aspect, provided are methods of producing a pharmaceutical composition comprising admixing a bispecific antibody as described herein and a pharmaceutically acceptable carrier. Methods of admixing an active ingredient with a pharmaceutically acceptable carrier are generally known in the art, for example, uniformly mixing the active compound(s) with liquids or finely divided solid carriers, or both, in the required proportions, and then, if necessary, forming the resulting mixture into a desired shape.

The following examples are provided to illustrate certain aspects of the present invention and to aid those of skill in the art in practicing the invention. These examples are in no way to be considered to limit the scope of the invention.

EXPERIMENTAL EXAMPLES

Example 1

Construction and Expression of an Anti-EGFR and Anti-VEGF Bispecific Antibody (Antibody 906)

CHO-K1-derived cell line, as the host cell line for antibody expression, was grown in CD-CHO suspension culture medium. The construction of bispecific antibody (referred to throughout as "Antibody 906") is described briefly as follows: the gene expression vector for bispecific antibody was generated by fusing an anti-VEGF scFv to the C terminus of an anti-EGFR antibody (referred to as "Antibody 206") heavy chain with molecular biology methods known in the arts. The molecular structure of the bispecific antibody is shown in FIG. 1A. The amino acid sequences of these chains are shown in Table 1.

Healthy mid-log CHO-K1 cells were pelleted by centrifuge and re-suspended in fresh CD-CHO media to achieve cell densities of approximately $1.43 \times 10^7$ cells/mL. 600 µL of cell suspension and 40 µg of linearized plasmid DNA were electroporated (Bio-rad GenePluser, single pulse 960 uFD, 300 V, 15-20 ms) and then diluted in 500 mL pre-warmed CD-CHO medium. Pipette 100 µL of diluted cells into each well of a 96-well plate to obtain $2 \times 10^3$ cells/well and 2-3 days later add 100 µL selection medium into each well. After 2-3 weeks the antibody expression level in the culture supernatant of clones isolated on 96-well tissue culture plates was determined by an enzyme-linked immunosorbent assay (ELISA). On the basis of the antibody titer in the supernatant, clones with high-level expression were transferred to 24-well plate containing suitable media. Specific antibody productivity (qAb) and specific growth rate (µ) were further analyzed by seeding cells at $2 \times 10^5$ cells per well containing 5 mL of medium in six-well tissue culture plates, culturing for 2 and 4 days, and usually 20-30 high-producing clones (parental clones) were transferred to shake flask for successive selection, and 5-8 highest producer clones were chosen for further subcloning, and antibody titer assay.

Figure 1B:
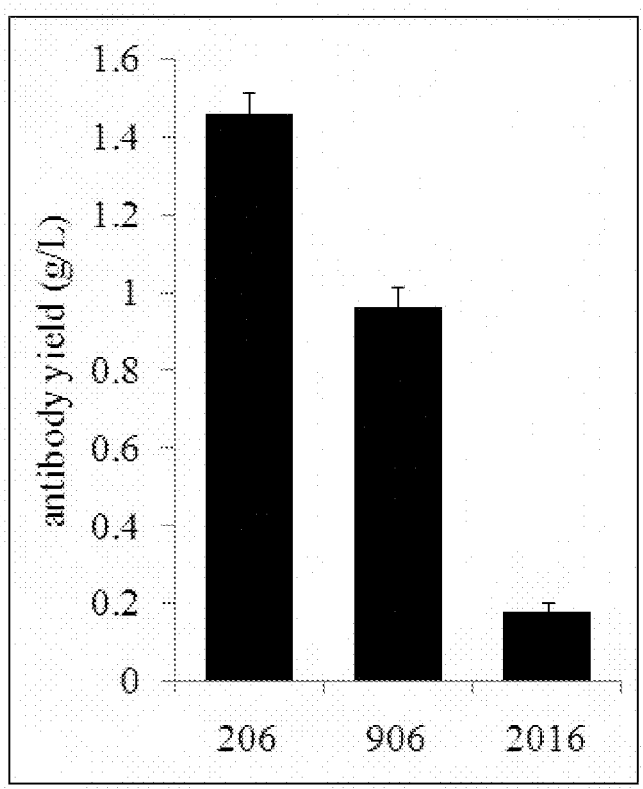
FIG. 1B shows the production level of Antibodies 206, 906 and 2016 in CHO cells.

The data showed that Antibody 906 was well expressed in CHO cells with average titers of over 1 g/L, much higher than a control antibody with identical format, (less than 0.2 g/L), although they shared the same construction and expression strategy. The average titers of Antibody 906 were compatible with its parental antibody, Antibody 206 (FIG. 1B) and 11-60 times higher than the reported antibody with similar structure (16-87 mg/L).

Example 2

Construction and Expression of an Anti-EGFR and Anti-CD3 Bispecific Antibody (Antibody 2016)

The construction of bispecific antibody (referred to throughout as "Antibody 2016") is described briefly as follows: the gene expression vector for bispecific antibody was generated by fusing an anti-CD3 scFv to the C terminus of an anti-EGFR antibody (referred to as "Antibody 206") heavy chain with molecular biology methods known in the arts. 600 µL of Healthy mid-log CHO-K1 cells and 40 µg of linearized plasmid DNA were electroporated (Bio-rad GenePluser, single pulse 960 uFD, 300 V, 15-20 ms) and then diluted in 500 mL pre-warmed CD-CHO medium. Pipette 100 µL of diluted cells into each well of a 96-well plate to obtain 2×10³ cells/well and 2-3 days later add 100 µL selection medium into each well. After 2-3 weeks the antibody expression level in the culture supernatant of clones isolated on 96-well tissue culture plates was determined by an enzyme-linked immunosorbent assay (ELISA). On the basis of the antibody titer in the supernatant, clones with high-level expression were transferred to 24-well plate containing suitable media. Specific antibody productivity (qAb) and specific growth rate (µ) were further analyzed by seeding cells at 2×10⁵ cells per well containing 5 mL of medium in six-well tissue culture plates, culturing for 2 and 4 days, and usually 20-30 high-producing clones (parental clones) were transferred to shake flask for successive selection, and 5-8 highest producer clones were chosen for further subcloning, and antibody titer assay. The data showed that the expression of Antibody 2016 was less than 0.2 g/L in CHO cells, much lower than the antibody 906 with identical format, although they shared the same construction and expression strategy.

Since the bispecific Antibody can target both T cells by anti-CD3 domain and tumor cells by anti-EGFR domain at the same times, it may not need the Fc domain to play an antibody-dependent cell-mediated cytotoxicity (ADCC) function. A bispecific Fab antibody was constructed by molecular biology method as above. The results showed this bispecific Fab antibody with the same strong tumor cytotoxicity as the full bispecific antibody in vitro.

Example 3

Purification of Antibody 906

Figure 2A:
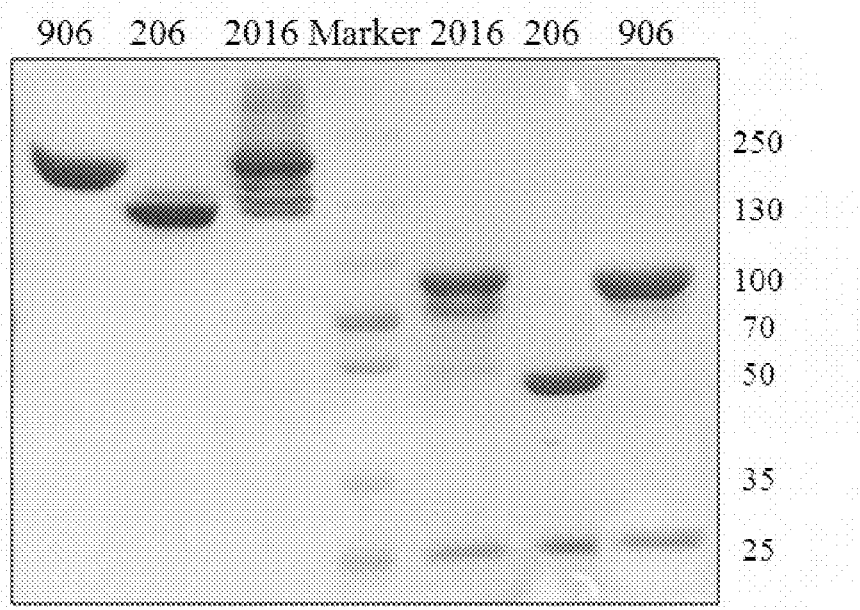
FIG. 2A shows the SDS-PAGE result of Antibody 206, 906 and 2016
Figure 2B:
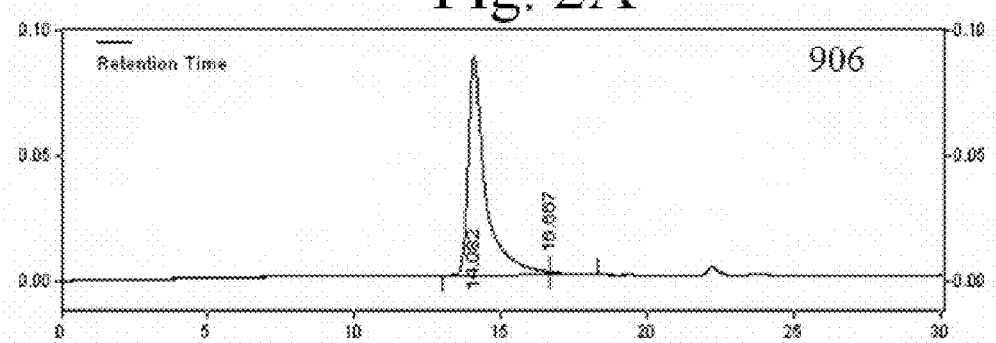
FIG. 2B shows the size-exclusion chromatography results of Antibody 906.

After 2 weeks large scale cell culture, the purification of bispecific antibody was carried out by centrifuging cell suspension and harvesting the supernatant, which was further cleared by centrifuging. Protein A affinity columns such as Mab Select SuRe (GE Healthcare) and ion exchange such as Capto S (GE) were used to purify the expressed antibodies. The product quality of the final purified bispecific antibody was assessed by SDS-PAGE and size-exclusion chromatography (SEC). SDS-PAGE analysis showed only a single protein band with the purified Antibody 906 under non-reducing condition, while control antibody with the same purification process contained severe aggregates (FIG. 2A). Further SEC analysis further demonstrated that Antibody 906 contained no aggregate (FIG. 2B). All these results showed that the sequence specificity of Antibody 906 could result its stable and high expression in mammalian cells.

Example 4

Differential Scanning Calorimetry (DSC) Assessment

Antibody 906 was analyzed by differential scanning calorimetry (DSC) on a VP-DSC capillary cell microcalorimeter (Microcal). The protein was analyzed at 1.0 mg/mL in 10 mM sodium citrate, 280 mM sucrose, pH 6.7. 4×400 µL samples of EI-04 were subjected to DSC analysis was (10-100° C., 120° C./h, 10 min pre-scan per sample, 8 second filtering period, low feedback mode). Raw data were analyzed using Origin7 software (OriginLab Corporation) and fit to determine the thermostabilities of the different immunoglobulin domains within the bispecific antibody. FIG. 3B showed that all three domains of Antibody 906 (scFv, CH2, Fab/CH3) unfolded cooperatively: the scFv variable domains unfolded at much lower temperatures with Tm=63° C.; The CH2 domain unfolded with a Tm=71° C. and the Fab/CH3 domain unfolded at a Tm=82.7° C. All these data demonstrated that the structure of Antibody 906 is highly stable since the lowest Tm among these domains was 63° C.

Example 5

Thermal Challenge Assays

100 µL purified antibodies (8 mg/mL) were heat-treated in PCR strip tubes for 90 min by a PCR thermocycler with a temperature gradient program (45-65° C.). Cooled samples were then centrifuged at 2,000 rpm, 4° C. for 20 min and supernatants were then assayed for binding to VEGF antigen by ELISA. 96-well plates were coated with 1 µg/mL antigen (VEGF for Antibody 906) in PBS at 4° C. overnight, and then blocked with PBS, 1% BSA, 0.05% Tween 20 for 1 h with shaking at room temperature. Test samples diluted in PBS (1:16000) were added to plates in a final volume of 100 µl, incubated overnight at 4° C. The next step consisted of a mouse anti-human IgG-horseradish peroxidase conjugate antibody incubated for 1 hour, and then washed 3 times with wash buffer (PBS, 0.05% Tween® 20), 100 µL of 3,3,5,5-tetramethylbenzidine (Sigma, St. Louis, Mo.) were added to each well, and upon color development, the reaction was stopped with 100 µL of 1 N sulfuric acid. Absorbance was measured using a VMax Kinetic Microplate reader (Molecular Devices, Sunnyvale, Calif.) at 450 nm and a blank at 630 nm. For thermal gradients, the data was analyzed with Prism 4 software (GraphPad Software, San Diego, Calif.) using a sigmoidal dose response with variable slope as the model. The values obtained for the mid-point of the thermal denaturation curves are referred to as $T_{50}$ values at which 50% of antibody molecules retained binding to relative antigen following thermal challenge and are not construed as being equivalent to biophysically derived Tm values. The results in FIG. 3A showed the affinity of Antibody 906 to VEGF antigen began to decrease at 56° C., and the T50 was 59.3° C. Antibody 906 showed high resistance to thermal challenge.

Example 6

Affinity Constant Determination by ELISA

Figures 4A, 4B:
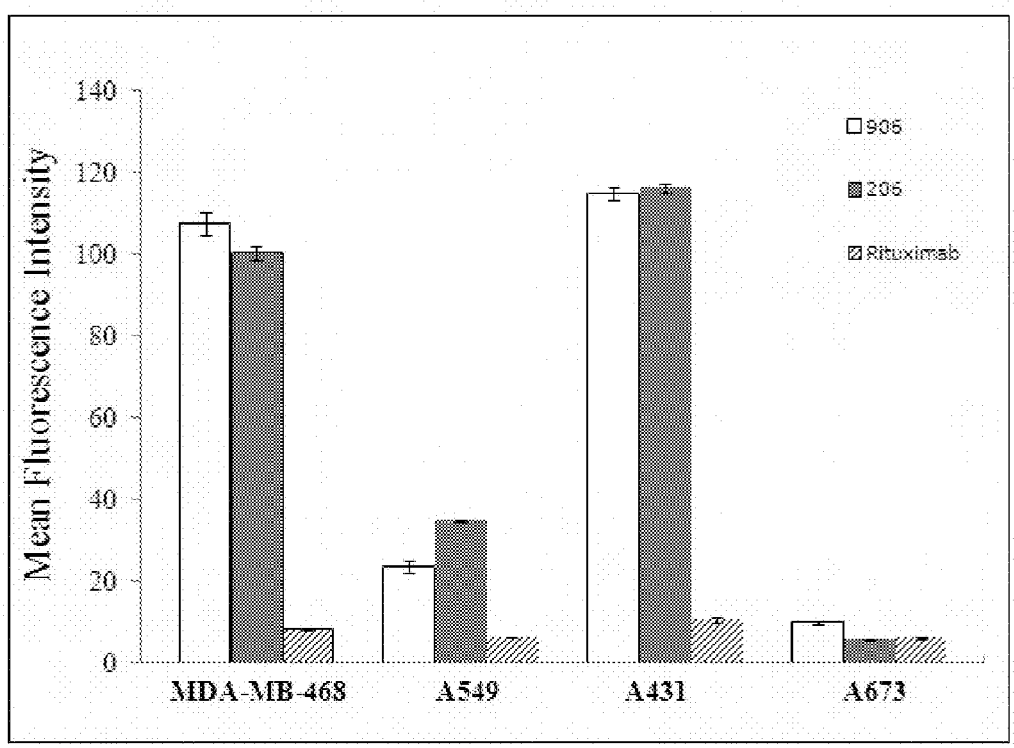
FIG. 4A depicts Antibody 906 binding affinity constants by ELISA.
FIG. 4B shows the result of the FACS-based direct EGFR binding assay for the tested Antibodies 906, 206 and Rituximab.

This example determined the affinity constant (Kaff) by ELISA. Briefly, three different concentrations of antigen (1 µg/mL, 2 µg/mL, 4 µg/mL) were coated onto 96-well plate in PBS at 4° C. overnight. After the plate was coated, blocking buffer (PBS, 1% BSA, 0.05% Tween® 20) was added and incubated at room temperature for 1 hour. Next, 100 µL of serial concentrations of antibody (starting concentration 1.25 µg/mL followed by 6 1:2 serial dilutions) were added to each well separately and incubated at 37° C. for 1 hour. The secondary step consisted of a mouse anti-human IgG-horseradish peroxidase conjugate antibody incubated for 1 hour, and then washed 3 times with wash buffer (PBS, 0.05% Tween 20), Subsequently, 100 µL of 3,3,5,5-tetramethylbenzidine (Sigma, St. Louis, Mo.) were added to each well, and upon color development, the reaction was stopped with 100 µL of 1 N sulfuric acid. Absorbance was measured using a VMax Kinetic Microplate reader (Molecular Devices, Sunnyvale, Calif.) at 450 nm and a blank at 630 nm. Sigmoid curves were constructed using the OD values obtained for different concentrations of each antibody. Three non-overlapping curves were selected for each antibody to calculate the affinity constant. The half maximum OD (OD-50) was assigned for all selected curves from which the corresponding antibody concentrations were extrapolated. Accordingly, Ab and Ab' were the measurable total antibody concentrations at OD-50 and OD'-50 for plates coated with Ag and Ag', respectively. The affinity constant was determined using the following equation (20): Kaff=(n−1)/2(n[Ab']t−[Ab]t) where t is temperature, n=[Ag]/[Ag']. Results demonstrated that Antibody 906 had affinity with both EGFR and VEGF. Compared with its parental antibody 206, the affinity of Antibody 906 to EGFR was decreased from $2.07 \times 10^9 M^{-1}$ to $5.7 \times 10^8 M^{-1}$, which might be resulted from the structure change; Compared with Bevacizumab, the affinity of Antibody 906 to VEGF was decreased from $6.59 \times 10^8 M^{-1}$ to $2.53 \times 10^8 M^{-1}$, almost no change (FIG. 4A).

Example 7

FACS-Based Direct EGFR Binding Assay of Tested Antibodies

Human breast carcinoma MDA-MB-468 cells, human epidermoid carcinoma A431 cell, human lung adenocarcinoma epithelial A549 cells, Human rhabdomyosarcoma A673 cells were cultured in DMEM with 10% FBS. Cells grown near confluence were lifted with 0.25% trypsin-EDTA and the trypsin digestion was then stopped by adding DMEM containing FBS. Cells were harvested by centrifugation at 800 rpm for 5 min, washed twice in PBS, counted and then resuspended at a density of $1 \times 10^6$ cells per tube. 300 μL diluted antibodies (10 μg/mL) were added into each tube. Samples were mixed and incubated on ice for 1 hour, then centrifuged at 800 rpm for 5 min at 4° C. and washed 2 times with PBS. The supernatant was aspirated and 100 μL of secondary antibody goat anti-human kappa-PE conjugate (Southern Biotech) at a 1:300 dilution was added to each corresponding well in FACS buffer. Samples were incubated for an additional 30 min on ice, and then washed as described above and resuspended in 100 μL PBS 4° C. Samples were analyzed on the FACSCalibur flow cytometer using CellQuest software (Becton Dickinson). Antibody 906 and 206 showed higher binding affinity to the cell lines that over express EGFR (MDA-MB-468 and A431), less binding affinity to A549 cells (medium EGFR expression) and no binding affinity to A673 cells (very low EGFR expression). A negative control, an anti-CD20 antibody, Rituximab, did not have EGFR binding affinity as predicted (FIG. 4B). Results demonstrated that Antibody 906 preserved the same binding affinity to EGFR as its parental Antibody 206.

Example 8

Cell Proliferation Inhibitory Assay

MDA-MB-468, A431, A549 and A673 cells were cultured in DMEM with 10% FBS. Cells grown near confluence were lifted with 0.25% trypsin-EDTA and the trypsin digestion was then stopped by adding DMEM containing FBS. Cells were harvested by centrifugation at 800 rpm for 5 min, counted and plated 100 μL at a density of 4000 cells per well in 96-well plate. 24 hours after seeding, 100 μL diluted antibody (starting concentration 15 μg/mL followed by ten 1:2 serial dilutions) was added into every well. After treated with antibodies for 72 hours, cells were analyzed for relative cell proliferation with 10 μL Cell Counting Kit-8 (CCK-8, DojindoMolec. Technologies, Japan) reagent. Among these four cell lines, MDA-MB-468 and A431 cell lines that over express EGFR showed higher sensitivity to the stimulation of Antibody 906 and 206 (FIGS. 5A&B). In comparison, A549 cells (medium EGFR expression and K-ras mutant) and A673 cells (very low EGFR expression) did not response to these antibodies (FIGS. 5C&D). Bevacizumab and the negative control Antibody Rituximab did not have any inhibitory effect on the proliferation of these four cells as predicted. These results indicated that Antibody 906 and 206 had the same cell proliferation inhibitory effect on EGFR-dependent cells.

Example 9

Pharmacokinetics Study of Antibody 906 in BALB/C Mice

Figure 6:
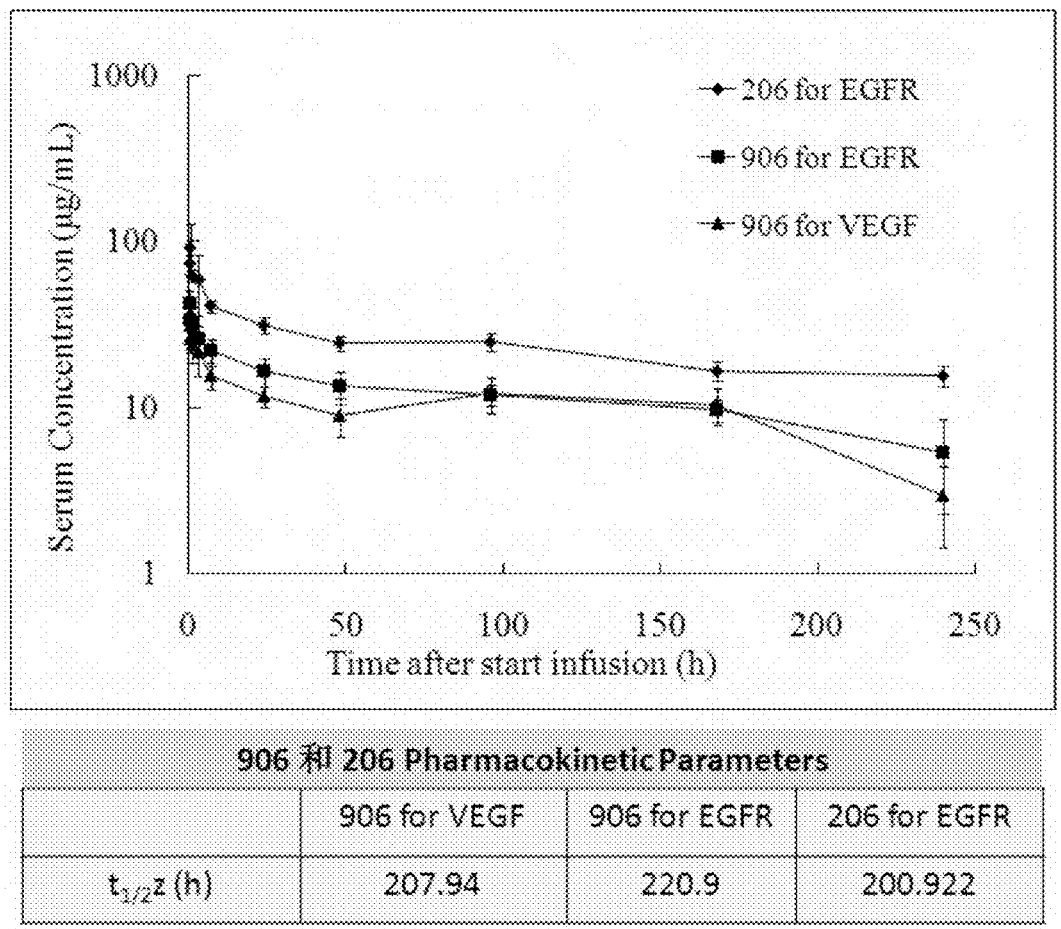
FIG. 6 depicts the pharmacokinetics study of Antibody 906 in BALB/C mice.

The pharmacokinetics studies of Antibody 906 and 206 were evaluated in BALB/C mice. BALB/C mice were administered 2 mg/kg tested antibody by tail vein injection. Blood samples were collected from each mouse via the saphenous vein at 0 h, 10 min, 30 min, 1 h, 3 h, 7 h, 24 h, 48 h, 96 h, 168 h and 240 h after injection. Blood was collected into heparin coated tubes followed by centrifugation (14,000 g, 3 minutes) to isolate plasma. Plasma concentrations of Antibody 906 and 206 were measured by ELISA (anti-EGFR for Antibody 206; anti-EGFR or VEGF for Antibody 906). Briefly, the ELISA consisted of the following steps: coating, blocking, sample binding, secondary antibody binding, color development and acid quench. In the plate coat step, EGFR or VEGF antigen was coated onto 96-well plate at 1 μg/mL in PBS at 4° C. overnight. After the plate was coated, blocking buffer (PBS, 1% BSA, 0.05% Tween 20) was added and incubated at room temperature for 1 hour. Next, 100 μL of standard or diluted plasma sample (1:200 diluted for anti-VEGF test: 1:500 diluted for anti-EGFR test) were added to triplicate wells for 1 hour at room temperature. The secondary step consisted of a mouse anti-human IgG-horseradish peroxidase conjugate antibody incubated for 1 hour, and then washed 3 times with wash buffer (PBS, 0.05% Tween 20), Subsequently, 100 μL of 3,3,5,5-tetramethylbenzidine (Sigma, St. Louis, Mo.) were added to each well, and upon color development, the reaction was stopped with 100 μL of 1 N sulfuric acid. Absorbance was measured using a VMax Kinetic Microplate reader (Molecular Devices, Sunnyvale, Calif.) at 450 nm and a blank at 630 nm. Noncompartmental pharmacokinetic parameters were calculated with WinNonlin (Pharsight, Mountain View, Calif.). Data showed that the half-life of an EGFR-binding component for 206 antibody was 200.92 hours, and the half-life of an EGFR-binding component for Antibody 906 was 220.9 hours, a VEGF-binding component for Antibody 906 was 207.94 hours (FIG. 6). Therefore Antibody 906 was very stale in mouse serum.

Example 10

Antibody 906 Eradicated Human A431 Tumor Xenografts

Figure 7A:
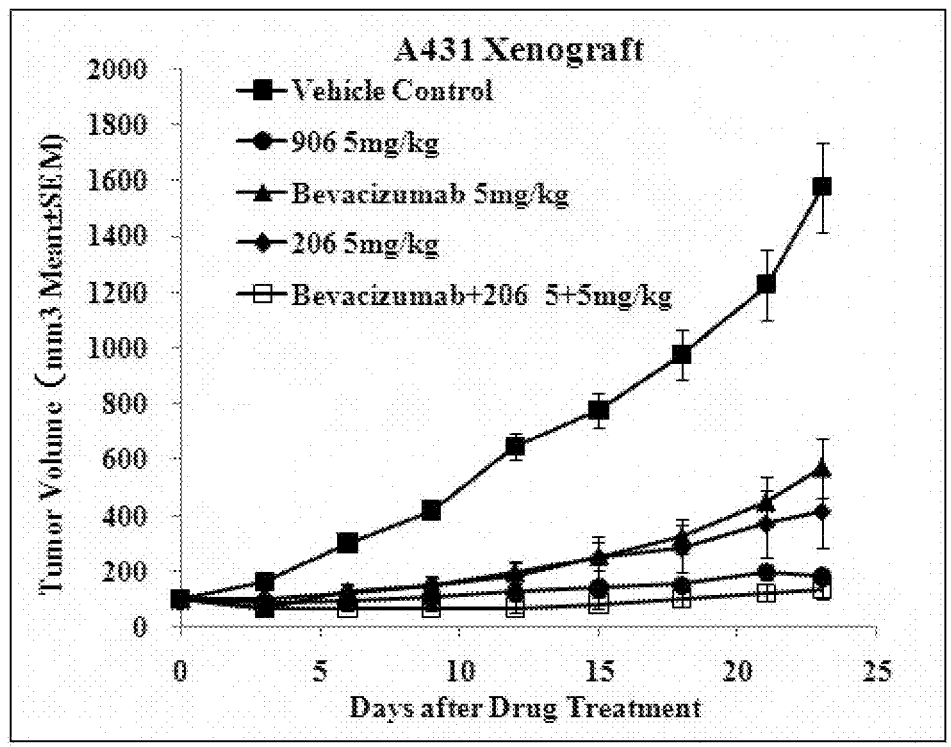
FIG. 7A shows Antibody 906 eradacated EGFR positive A431 tumor xenographs.

In Vivo Tumor Studies: The effects of Antibody 906 on the growth of established tumors were examined on human A431 tumor xenografts. Human A431 cells (ATCC, CRL-7907) were cultured in DMEM medium supplemented with 10% FBS, 2 mM glutamine and antibiotics. Female BALB/c nude mice, 4-6 weeks old, were injected subcutaneously with 4×10⁶ tumor cells in the dorsal area in a volume of 100 µL. When the tumor xenografts reaches a size of 80-200 mm³ (calculated as 0.5 (length×width²)), animals were then treated with Antibody 906, 206 antibody, Bevacizumab, 206 antibody combined with Bevacizumab or a control buffer. All antibodies were administered at the doses of 5 mg/kg. Animals were dosed every 3 days for a total of 8 doses i.p. in a volume of 100 µl. Each group consisted of 12 mice. Tumor size was determined at 3 days intervals. Twenty four days after tumor cell inoculation, animals were euthanized and tumors were removed and weighed. As shown in FIG. 7A, at 5 mg/kg dose tested, Antibody 906 and 206 antibody combined with Bevacizumab markedly suppressed tumor growth 24 days after drug treatment and the treatment better than either 206 antibody or Bevacizumab.

Example 11

Antibody 906 Eradicated Human A673 Tumor Xenografts

Figure 7B:
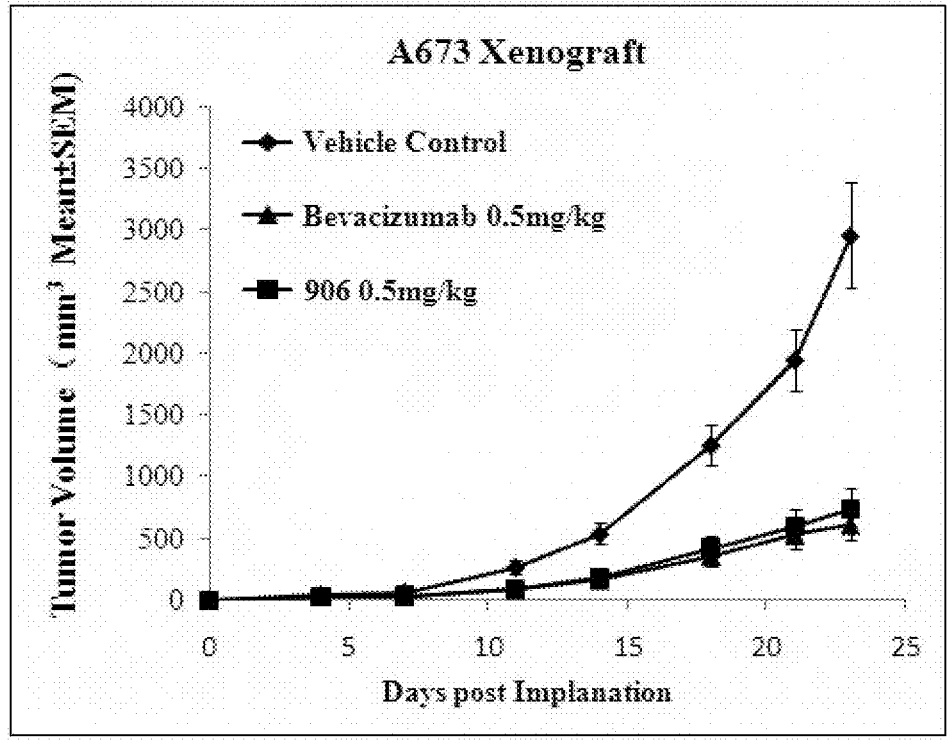
FIG. 7B shows Antibody 906 eradicated EGFR negative A673 tumor xenographs.

In Vivo Tumor Studies: The effects of Antibody 906 on the growth of established tumors were examined on human A673 tumor xenografts. Human A673 cells (ATCC) were cultured in DMEM medium supplemented with 10% fetal bovine serum, 2 mM glutamine and antibiotics. Female BALB/c nude mice, 4-6 weeks old, were injected subcutaneously with 2×10⁶ tumor cells in the dorsal area in a volume of 100 µL. In 24 hours, animals were treated with Antibody 906, Bevacizumab, or a control buffer. All antibodies were administered at the doses of 0.5 mg/kg. Animals were dosed 3 times per a week for a total of 9 doses i.p. in a volume of 100 µl. Each group consisted of 9 mice. Twenty four days after tumor cell inoculation, animals were euthanized and tumors were removed and weighed. As shown in FIG. 7B, at 0.5 mg/kg dose tested, Antibody 906 and bevacizumab markedly suppressed tumor growth 24 days after drug treatment.

Example 12

Endothelial Cell Proliferation Assay for Antibody 906

Figure 8:
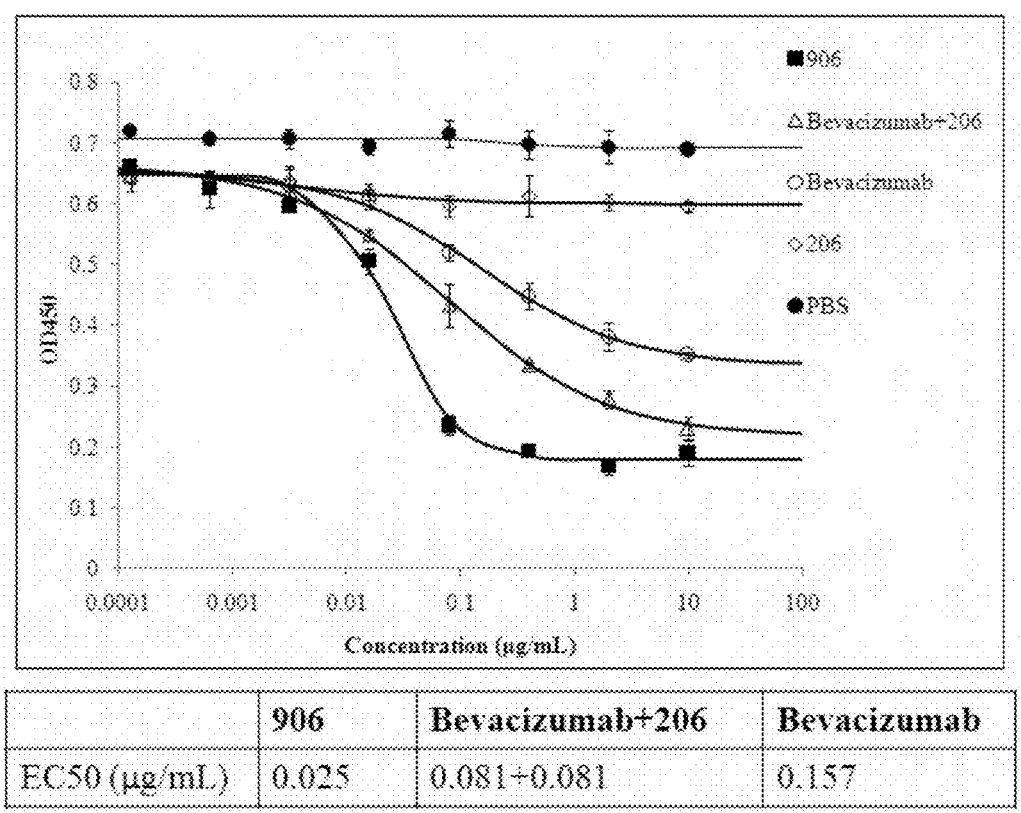
FIG. 8 shows the HUVEC cell proliferation inhibitory assay result of Antibody 906.

This example further determined the activity of Antibody 906 in inhibiting VEGF-stimulated growth of HUVECs. HUVECs were seeded at a density of 5,000 cells/well in 96-well plates. A total of 50 ml of the tested antibodies at indicated concentrations were pre-incubated with 50 ml VEGF (30 ng/ml) for 1 hour before added to plates and incubated in DMEM with 10% FBS at 37° C., 5% CO₂ for 72 hours. Then 10 µL Cell Counting Kit-8 (CCK-8, DojindoMolec. Technologies, Japan) reagent was added to each well and incubated for an additional 8 hours. Cell viability was measured with. All studies were conducted twice and in triplicates for each sample concentration. Results showed that both Antibody 906 and Bevacizumab antibodies displayed dose-dependent inhibition on HUVEC growth (FIG. 8). Antibody 906 (EC50=0.025 µg/mL) was about 5-fold more potent than Bevacizumab (0.157 µg/mL).

Example 13

Conjugation of Antibody 906 with SMCC-DM1

Figure 9:
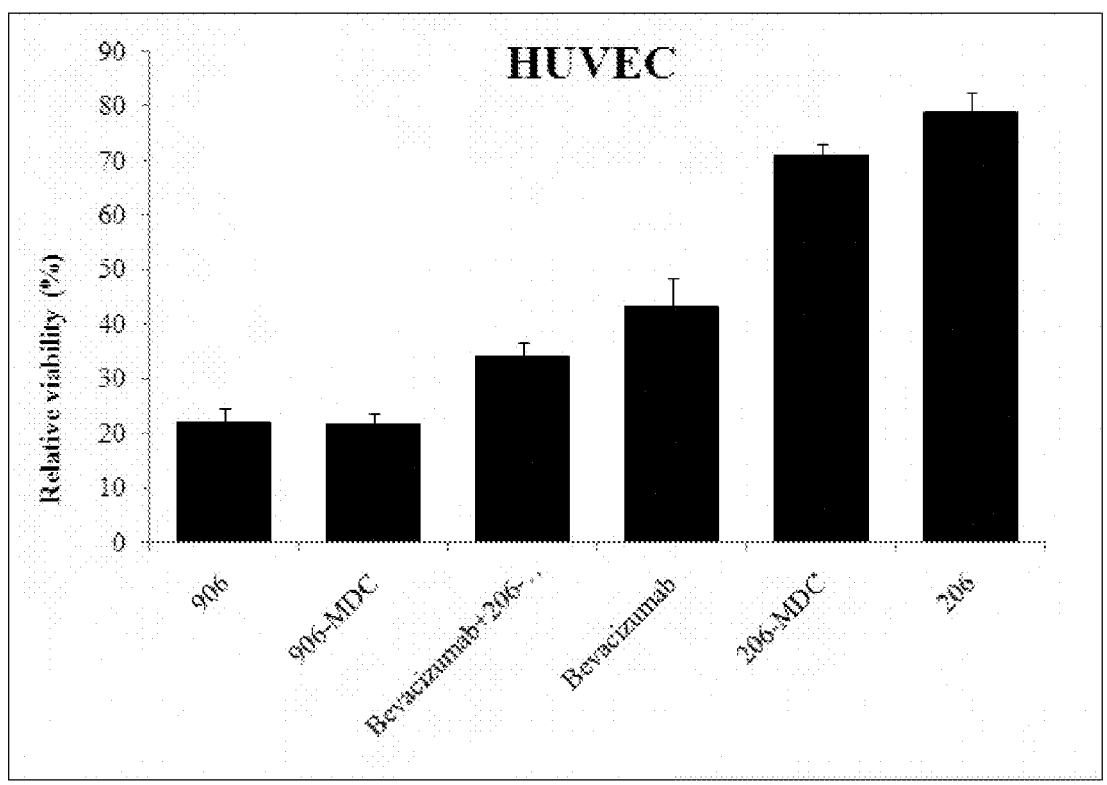
FIG. 9 shows the HUVEC cell proliferation inhibitory assay result of Antibody 906-SMCC-MD1.

The drug-linker SMCC-DM1 was prepared in the following reactions: 3-mercaptopropanoic acid (MPr) was reacted with N-succinimidyl 4-(maleimidomethyl)cyclohexane-1-carboxylate (SMCC) in the presence of N,N-diisopropylethylamine (DIEA), giving the MPr-SMCC at a yield of over 95%; condensation of N-Me-L-Ala-DM1, which was prepared by deprotection of Fmoc-N-Me-Ala-DM1 under a base piperidine in CH₃CN, with MPr-SMCC in the presence of a coupling reagent EDC, giving the desired coupled product SMCC-DM1 in 60-70% yield over two steps. Antibody 906 was diluted to 2.5 mg/mL in solution A (50 mM potassium phosphate, 50 mMNaCl, and 2 mM EDTA, pH 6.5). SMCC-DM1 was added to give a ratio of SMCC-DM1 to antibody of 7:1 mole equivalent. Then dimethylacetamide (DMA) was added to 15% (v/v) to the reaction and reaction was mixed by stirring for 4 h at ambient temperature. D-Lmcc-Bat0 Antibody 906 conjugate was purified from excess unreacted or hydrolyzed reagent and excess SMCC-DM1 using a G25 gel filtration column equilibrated in pH 7.4 phosphate buffer (aqueous). The conjugate was then dialyzed overnight into pH 7.4 phosphate buffer (aqueous) and filtered through a 0.22 m filter for final storage. The method of site-specific conjugation of a cytotoxic drug to an antibody is briefly described as follows: intact 906 MAbs were diluted to 1 mg/mL with 150 mM phosphate buffer, pH 7.0. Antibodies were reduced with a final concentration of 20 mM DTT at 25° C. for 30 minutes. The reaction resolution were loading, Separation of heavy chain and light chain were achieved using 7.8×300 mm Zenix™ SEC-300 columns. The method of conjugation of a cytotoxic drug to light chain is the same to the intact Mabs, The separated heavy chain were loading to protein A column for protein A can fix the heavy chain. Eluting the non-binding fragment and the reaction solution for light chain conjugate were loading. On-column refolding were performed. The elution was using the Gly-HCL (0.1 mM, pH 3.0) buffer. The elution solution was then dialyzed overnight into pH 7.4 phosphate buffer (aqueous) and filtered through a 0.22 m filter for final storage. The number of SMCC-DM1 molecule per antibody molecule in the final conjugate was measured by determining absorbance of the conjugate at 252 and 280 nm and using known extinction coefficients for SMCC-DM1 and antibody at these two wavelengths. A ratio of maytansinoid compound to antibody of 3.8:1.0 was normally obtained. Considering very small amount of EGFR protein expression in HUVEC cells, the 906-MDC conjugates will not show any stronger effect than the 906 antibody in the HUVEC model, the experimental results showed that when the test antibody concentration was 0.4 µg/mL, the 906-MDC conjugates had the same HUVEC cell growth inhibition effects as 906 antibodies, consistent with the expected (FIG. 9)

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

The invention claimed is:

1. A bispecific antibody that binds EGFR and VEGF and comprises two light chains comprising the amino acid sequence of SEQ ID NO: 1 and two heavy chains comprising the amino acid sequence of SEQ ID NO: 2.

2. A composition comprising a first polypeptide that binds EGFR and comprises the amino acid sequence of SEQ ID NO: 1 and a second polypeptide that binds EGFR and VEGF and comprises the amino acid sequence of SEQ ID NO: 2.

* * * * *

SEQUENCE LISTING

<160> NUMBER OF SEQ ID NOS: 14

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 712
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Glu Ser Gly Pro Gly Leu Val Lys Pro Ser Glu Thr Leu
1               5                   10                  15

Ser Leu Thr Cys Thr Val Ser Gly Gly Ser Val Ser Ser Gly Asp Tyr
            20                  25                  30

Tyr Trp Thr Trp Ile Arg Gln Ser Pro Gly Lys Gly Leu Glu Trp Ile
        35                  40                  45

Gly His Ile Tyr Tyr Ser Gly Asn Thr Asn Tyr Asn Pro Ser Leu Lys
    50                  55                  60

Ser Arg Leu Thr Ile Ser Ile Asp Thr Ser Lys Thr Gln Phe Ser Leu

```
                65                  70                  75                  80
Lys Leu Ser Ser Val Thr Ala Ala Asp Thr Ala Ile Tyr Tyr Cys Val
                    85                  90                  95

Arg Asp Arg Val Thr Gly Ala Phe Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Gly Ser Gly Gly Gly Gly Ser Glu Val
    450                 455                 460

Gln Leu Val Glu Ser Gly Gly Leu Val Gln Pro Gly Gly Ser Leu
465                 470                 475                 480

Arg Leu Ser Cys Ala Ala Ser Gly Tyr Asp Phe Thr His Tyr Gly Met
                485                 490                 495
```

Asn Trp Val Arg Gln Ala Pro Gly Lys Cys Leu Glu Trp Val Gly Trp
            500                 505                 510

Ile Asn Thr Tyr Thr Gly Glu Pro Thr Tyr Ala Ala Asp Phe Lys Arg
        515                 520                 525

Arg Phe Thr Phe Ser Leu Asp Thr Ser Lys Ser Thr Ala Tyr Leu Gln
    530                 535                 540

Met Asn Ser Leu Arg Ala Glu Asp Thr Ala Val Tyr Tyr Cys Ala Lys
545                 550                 555                 560

Tyr Pro Tyr Tyr Tyr Gly Thr Ser His Trp Tyr Phe Asp Val Trp Gly
                565                 570                 575

Gln Gly Thr Leu Val Thr Val Ser Ser Gly Gly Gly Gly Ser Gly Gly
            580                 585                 590

Gly Gly Ser Gly Gly Gly Gly Ser Gly Gly Gly Gly Ser Asp Ile Gln
            595                 600                 605

Leu Thr Gln Ser Pro Ser Ser Leu Ser Ala Ser Val Gly Asp Arg Val
        610                 615                 620

Thr Ile Thr Cys Ser Ala Ser Gln Asp Ile Ser Asn Tyr Leu Asn Trp
625                 630                 635                 640

Tyr Gln Gln Lys Pro Gly Lys Ala Pro Lys Val Leu Ile Tyr Phe Thr
                645                 650                 655

Ser Ser Leu His Ser Gly Val Pro Ser Arg Phe Ser Gly Ser Gly Ser
            660                 665                 670

Gly Thr Asp Phe Thr Leu Thr Ile Ser Ser Leu Gln Pro Glu Asp Phe
        675                 680                 685

Ala Thr Tyr Tyr Cys Gln Gln Tyr Ser Thr Val Pro Trp Thr Phe Gly
    690                 695                 700

Cys Gly Thr Lys Val Glu Ile Lys
705                 710

<210> SEQ ID NO 3
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Ala
            210

<210> SEQ ID NO 4
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 5
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Glu Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 6
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Pro
    210                 215                 220

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

```
Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 8
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
 50                 55                  60

Lys Arg Arg Phe Thr Phe Ser Leu Asp Thr Ser Lys Ser Thr Ala Tyr
 65                 70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
 1               5                  10                  15

Asp Arg Val Thr Ile Asn Cys Gln Ala Ser Gln Ser Ile Tyr Asn Asn
            20                  25                  30

Asn Glu Leu Ser Trp Tyr Gln Gln Lys Pro Gly Lys Pro Pro Lys Leu
        35                  40                  45

Leu Ile Tyr Arg Ala Ser Thr Leu Ala Ser Gly Val Pro Ser Arg Phe
 50                 55                  60

Ser Gly Ser Gly Ser Gly Thr Asp Phe Thr Leu Thr Ile Ser Ser Leu
 65                 70                  75                  80

Gln Pro Glu Asp Val Ala Thr Tyr Tyr Cys Gly Gly Tyr Lys Ser Tyr
                85                  90                  95
```

```
Ser Asn Asp Gly Asn Gly Phe Gly Gly Gly Thr Lys Val Glu Ile Lys
            100                 105                 110
```

<210> SEQ ID NO 10
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Asn
            20                  25                  30

Asp Val Met Cys Trp Val Arg Gln Ala Pro Gly Lys Gly Leu Glu Trp
        35                  40                  45

Ile Gly Cys Ile Met Thr Thr Asp Val Val Thr Glu Tyr Ala Asn Trp
    50                  55                  60

Ala Lys Ser Arg Phe Thr Val Ser Arg Asp Ser Ala Lys Asn Ser Val
65                  70                  75                  80

Tyr Leu Gln Met Asn Ser Leu Arg Ala Glu Asp Thr Ala Val Tyr Phe
                85                  90                  95

Cys Ala Arg Asp Ser Val Gly Ser Pro Leu Met Ser Phe Asp Leu Trp
            100                 105                 110

Gly Pro Gly Thr Leu Val Thr Val Ser Ser
        115                 120
```

<210> SEQ ID NO 11
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Val Tyr Thr Phe Gly Gln Gly Thr Lys Leu Glu Ile Lys Arg
            100                 105                 110
```

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Ser Trp Tyr Tyr Trp Tyr Phe Asp Leu
            100                 105                 110

Trp Gly Arg Gly Thr Leu Val Thr Val Ser Ser
            115                 120

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Leu His Trp Val Arg Gln Ala Pro Gly Lys Gly Leu Glu Trp Val
        35                  40                  45

-continued

```
Ala Gly Ile Thr Pro Ala Gly Gly Tyr Thr Tyr Tyr Ala Asp Ser Val
    50              55                  60

Lys Gly Arg Phe Thr Ile Ser Ala Asp Thr Ser Lys Asn Thr Ala Tyr
65              70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
                100             105                 110

Gly Thr Leu Val Thr Val Ser Ser
            115             120
```